United States Patent
Waterbury et al.

(10) Patent No.: US 6,835,754 B2
(45) Date of Patent: Dec. 28, 2004

(54) USE OF ARYL NITRONE COMPOUNDS IN METHODS FOR TREATING NEUROPATHIC PAIN

(75) Inventors: L. David Waterbury, San Carlos, CA (US); Paul L. Wood, Morgan Hill, CA (US); M. Amin Khan, Morgan Hill, CA (US); Ravindra B. Upasani, San Jose, CA (US)

(73) Assignee: Renovis, Inc., San Francisco, CA (US)

( * ) Notice: Subject to any disclaimer, the term of this patent is extended or adjusted under 35 U.S.C. 154(b) by 0 days.

(21) Appl. No.: 10/043,659

(22) Filed: Jan. 8, 2002

(65) Prior Publication Data

US 2002/0165274 A1 Nov. 7, 2002

Related U.S. Application Data

(60) Provisional application No. 60/260,469, filed on Jan. 8, 2001.

(51) Int. Cl.[7] .................. A61K 31/14; A61K 31/075
(52) U.S. Cl. .................. 514/643; 514/642; 514/720
(58) Field of Search ................. 514/643, 642, 514/720, 579, 715, 717; 569/50

(56) References Cited

U.S. PATENT DOCUMENTS

| | | |
|---|---|---|
| 3,666,754 A | 5/1972 | Miami et al. |
| 3,834,073 A | 9/1974 | Dorschner et al. |
| 3,849,934 A | 11/1974 | Dorschner et al. |
| 3,903,049 A | 9/1975 | Saltman et al. |
| 3,917,700 A | 11/1975 | Auerbach |
| 4,362,719 A | 12/1982 | Cavazza |
| 5,292,746 A | 3/1994 | Carr et al. |
| 5,352,442 A | 10/1994 | Proctor |
| 5,397,789 A | 3/1995 | Carr et al. |
| 5,455,272 A | 10/1995 | Janzen et al. |
| 5,532,252 A | 7/1996 | Carr et al. |
| 5,723,502 A | 3/1998 | Proctor |
| 6,046,232 A | 4/2000 | Kelleher et al. |
| 6,342,523 B1 * | 1/2002 | Waterbury et al. |
| 6,433,008 B1 | 8/2002 | Kelleher et al. |
| 6,441,032 B1 | 8/2002 | Kelleher et al. |

FOREIGN PATENT DOCUMENTS

| | | |
|---|---|---|
| EP | 0 327 263 | 9/1994 |
| GB | 2137619 | 10/1984 |
| WO | WO 91/05552 | 5/1991 |
| WO | WO 92/22290 | 12/1992 |
| WO | WO 95/17876 | 7/1995 |
| WO | WO 97/19054 | 5/1997 |
| WO | WO 98/13332 | 4/1998 |
| WO | WO 00/32567 | 6/2000 |

OTHER PUBLICATIONS

Harrison's Principles of Internal Medicine, 13th ed., 1993, p. 2378.*

(List continued on next page.)

Primary Examiner—San-Ming Hui
(74) Attorney, Agent, or Firm—Burns, Doane, Swecker & Mathis, L.L.P.

(57) ABSTRACT

3,4,5-trisubstituted aryl nitrone compounds having the formula:

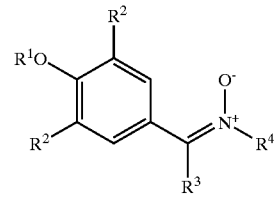

where $R^1$–$R^4$ are as defined in the specification are useful as therapeutics for neuropathic pain conditions in mammals.

16 Claims, 6 Drawing Sheets

OTHER PUBLICATIONS

Kontani et al., New England Journal of Medicine, 2000; 343: 1514–1519.*
Besson, et al., *Nonlinear Optics*, vol. 4, pp. 181–190 (1993).
Proctor, P., *Physiol. Chem. & Physics*, vol. 4, pp 349–360 (1974).
Proctor, P., et al., *Physio. Chem. & Physics and Medical NMR*, vol. 16, pp. 175–195 (1984).
Proctor, P., *CRC Handbook of Free Radicals and Antioxidants*, vol. 1, pp. 209–221.
CA:87:99910 abstract of J. Endocrinol by Vaughan et al. 73(3) pp. 40P(02)–41P. (1977).
CA:102:5798 Liebigs Ann Chem., 9, pp. 1545–1562 (1984) by Kliegel.
CA: 107:115572 abstract of Huaxue Xuebao by Chem 44 (9) pp 927–933.
CA: 109:149392 abstract of Synthesis by Kloc 12 pp 1084–1087.
CA: 116:193591 abstract of J. Org. Chem. by Hinton 57(9) pp 2646–2651.
CA:122:160222 abstract of J. Chem. Soc., 1(23) pp. 3353–3354 by Sivasobramanien.
CA:122:31336 abstract of WO 94/22831 Oct. 1994.
CA:127:80093 abstract of Nippon Naibunpi Gakkai Zasshi by Zkonno 73(3) pp. 451–461 (1997).
CA:130:217477 abstract of Lupus by Dooley 7(9) pp. 630–634 (1998).
CA: 130:280743 abstract of Eur. J. Immunol. by Scotet 29(3) pp 973–985.
CA:130:291586 abstract of AU 695664 Mar. 1996.
CA: 130:89983 abstract of Ziekenuisfarmacie by De Jong van den Berg 14(4) pp 190–193.
Chem. abs Acension No. 1995:549812 abs of J. Clin Endocrinol Metab 80(5) by Smith pp. 1502–1505 (1995).
Acession No. 1999–397013 abs of Graefe's Arch. Clin. Exp. Ophthalmol. 237(6) pp 508–512.
STN Information Services (1999), Ref. No. XP–002090680.
Bennett, G.J., et al., "A Peripheral Mononeuropathy in Rate that Produces Disorders of Pain Sensation Like those Seen in Man", *Pain*, vol. 33, pp. 87–107 (1988).
DeGray, et al., "Biological Spin Trapping", *Electron Spin Resonance*, vol. 14, pp. 246–300 (1994).
Dornan, et al, "Bilateral Injections of BA(25–35)+IBO into the Hippocampus Disrupts Acquisition of Spatial Learning in the Rat", *NeuroReport*, vol. 5, pp. 165–168 (1993).
Eddy, et al., "Synthetic Analgesics. II. Dithienylbutenl–And Dithienylbutulamines", *Pharm. Ep. Ther.*, vol. 107, pp. 385–393 (1953).

Forster, et al., "Age Differences in Acquisition and Retention of One–Way Avoidance Learing in C57BL/6NNia and Autoimmunce Mice", *Beha. Neural. Biology*, vol. 49, pp. 139–151 (1988).
Glenner, et al., "Alzheimer's Disease: Initial Report of the Purification and Characterization of a Novel Cerebrovascular Amyloid Protein", *Biochem. Biophys. Res. Commun.*, vol. 120, pp. 885–890 (1984).
Maples, K.R., et al., "In Vivo Detection of Free Radical Metabolites", *Free Radicals in Synthesis and Biology* (F. Misci, ed.), pp. 423–436 (1989).
McFarlin, D.E., "Recurrent Experimental Allergic Encephalomyelitis in the Lewis Rat", *The J. of Immun.*, vol. 113, No. 2, pp. 712–715 (1974).
Setlzer, Z., et al., "A Novel Behavioral Model of Neuropathic Pain Disorders Produced in Rates by Partial Sciatic Nerve Injury", *Pain*, vol. 43, pp. 205–218 (1990).
Tanzi, R.E., "Molecular Genetics of Alzheimer's Disease and the Amyloid B Peptide Precursor Gene", *Ann. Med.*, vol. 21, pp. 91–94 (1989).
Waage, A., et al., "Local Production of Tumor Necrosis Factor α, Interleukin 1, and Interleukin 6 in Meningococcal Meningitis", *J. Exp. Med.*, vol. 170, pp. 1859–1867 (1989).
Whitehause, P.J., et al., "Alzheimer's Disease and Senile Dementia: Loss of Neurons in the Basal Forebrain", *Science*, vol. 215, pp. 1237–1239 (1982).
Yan, S.D., et al., "Amyloid–β Peptide–Receptor for Advanced Clycation Endproduct Interaction Elicits Neuronal Expression of Macrophage–Colony Stimulating Factor: A Proinflmmatory pathway in Alzheimer Disease", *Proc. natl. Acad. Sci.*, vol. 94, pp. 5296 (1997).
CA:100:138667 abs of Liebigs Ann Chem 11 pp. 1937–1949. (1984).
CA: 111:58194 abs of Chem. Express by Kotake 3(12) pp 715–718. (1989).
CA: 119:179060 abs Clin. Immunol. Immunopathol. by Dilvani 67(3 Pt 1) pp 199–203.
CA: 124:160227 abs of J. Chem. Soc. Perkin Trans. 1 by Sivasubramanian 23 pp 3353–4.
CA:124:200109 abs of Cirology by Algright 217(1) pp. 211–219 (1996).
CA: 131:85 abs of Drugs Aging by Durif 14(5) pp. 337–345 (1999).
CA:130:217477 abs of Lupus by Dooley et al. 7(9) pp. 630–634 (1998).

* cited by examiner

USE OF ARYL NITRONE COMPOUNDS IN METHODS FOR TREATING NEUROPATHIC PAIN

This application claims priority under 35 U.S.C. § 119 to U.S. Provisional Application No. 60/260,469 entitled and filed on USE OF ARYL NITRONE COMPOUNDS IN METHODS FOR TREATING NEUROPATHIC PAIN filed on Jan. 8, 2001, the entire content of which is hereby incorporated by reference.

BACKGROUND OF THE INVENTION

1. Field of the Invention

This invention relates to the use of aryl nitrone compounds as therapeutic agents for the treatment of neuropathic pain in mammals.

2. State of the Art

Neuropathic pain is a category of chronic pain that has been widely studied. Neuropathic pain occurs when the peripheral and/or central nervous systems are sensitized following an injury to the peripheral system. This initial injury can occur from a wide variety of causes including traumatic physical injury, as well as systematic diseases such as diabetes, herpes zoster, AIDS/HIV, syphilis and various other autoimmune diseases.

Examples of pain syndromes of this class include post hepatic neuralgia, neuritis, temporomandibular disorder, myofascial pain, back pain, pain induced by inflammatory conditions. Neuropathic pain may occur in all body regions. Thus, neuropathic pain may e.g., originate from the dental region. Burn injury also often leads to neuropathic hyperalgesia in the affected body area. Neuralgia is characterized, in its acute phase, by intraneural inflammation which can cause damage to primary afferent axons, this inducing neuropathic pain. Neuropathic pain may also be induced by diabetic conditions (diabetic neuropathy). Neuropathy of primary afferent axons in long nerves is found in diabetic patients. Nociceptor sensitization may ensue.

The following more complete listing of pain conditions included within the definition of neuropathic pain may be found in PAIN MANAGEMENT, Rochelle Wagner and Robert R. Myers.

Examples and Causes of Neuropathic Pain

| Peripheral nerve trauma | Spinal cord |
| --- | --- |
| Entrapment neuropathy | Trauma, transaction, hemisection, |
| Nerve transection, including surgery | Lissauer tract section |
| Causalgia | Syrinx |
| Amputation and stump pain | Mutiple sclerosis |
| Neuroma | Tumor compression |
| Post-choracotomy pain | Arteriovenous malformation |
| Other mononeuropathies | Dyscraphism |
| Diabetic | Vitamin B12 deficiency |
| Malignant nerve/plexus invasion | Hematomyelia |
| Plexus irradiation | Syphilitic myelitis |
| Ischemic irradiation | Commissural myelotomy |
| Connective tissue disease | Brain stem |
| (rheumatoid arthritis, systemic lupus erythematosus, polyarteritis nodosa) | Wallenberg's syndrome Multiple sclerosis Tuberculoma |
| Polyneuropathies | Tumor |
| Diabetic | Syrinx |
| Alcoholic | Thalamus |
| Nutritional | Infarction |
| Amyloid | Tumor |
| Fabry disease | Surgical lesions in main sensory necleus |
| Chemical (e.g., anticancer therapies) | |
| Idiopathic | Hemorrahage |
| AIDS neuropathy | Corrical/subcorrical |
| Root and dorsal root ganglion | Infarction |
| Prolapsed disk/compression | Trauma |
| Postherpetic or trigeminal neuralgia | Tumor |
| Arachnoiditis | Arteriovenous malformation |
| Root avulsion | |
| Tumor compression | |
| Surgical rhizotomy | |

Neuropathic pain conditions are characterized by hyperesthesia (enhanced sensitivity to a natural stimuli), hyperalgesia (abnormal sensitivity to pain), allodynia (widespread tenderness, characterized by hypersensitivity to tactile stimuli) and/or spontaneous burning pain. In humans, neuropathic pains tend to be chronic. Neuropathic pain is generally considered to be nonresponsive or only partially responsive to conventional opioid analgesic regimens. Treatment which work with neuropathic pain are often nonhelpful in other pain conditions. Consequently, alternate therapies for the management of neuropathic pain are widely sought.

The present invention provides compositions and methods for treating these forms of neuropathic pain. These compositions and methods employ 3,4,5-trisubstituted arylnitrone compounds as their active agents. Many of the compounds themselves have already been disclosed in commonly-owned U.S. Patent Application Ser. No. 60/110, 541 (filed 2 Dec. 1998) and PCT Application WO 0032567 (published 8 Jun. 2000). Other compounds were disclosed in U.S. Pat. No. 5,455,272.

SUMMARY OF THE INVENTION

In accord with this invention, pain, particularly neuropathic pain as described above, is treated by administering to a patient suffering from such pain an effective, pain-treating amount of one or more 3,4,5-trisubstituted aryl nitrone compounds.

Accordingly, in one aspect, this invention is directed to administering to a neuropathic pain sufferer one or more compounds of formula I:

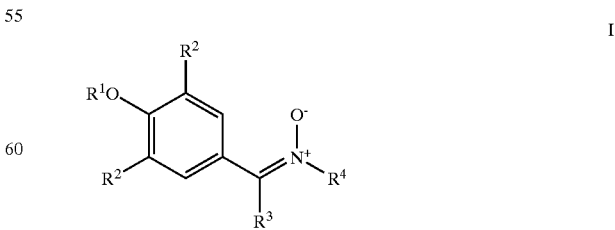

wherein $R^1$ is selected from the group consisting of hydrogen, alkyl

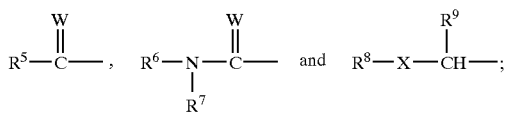

each $R^2$ is independently selected from a group of the formula:

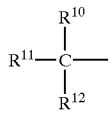

$R^3$ is selected from the group consisting of hydrogen, alkyl, cycloalkyl and aryl;

$R^4$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^5$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^6$ and $R^7$ are independently selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^6$ and $R^7$ can be joined to form an alkylene or substituted alkylene group having from 2 to 10 carbon atoms;

$R^8$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^8$ and $R^9$ can be joined to form an alkylene or substituted alkylene group having from 2 to 10 carbon atoms;

$R^{10}$ is selected from the group consisting of hydrogen, lower alkyl and lower cycloalkyl; or $R^1$ and $R^{10}$ can be joined to form an alkylene, substituted alkylene, —C(O)— —S(O)— or —S(O)$_2$— group;

$R^{11}$ and $R^{12}$ are independently selected from the group consisting of lower alkyl and lower cycloalkyl; or $R^{11}$ and $R^{12}$ can be joined to form an alkylene group having from 2 to 10 carbon atoms;

X is oxygen, sulfur, —S(O)— or —S(O)$_2$—; and

W is oxygen or sulfur; and pharmaceutically-acceptable salts thereof.

Preferably, $R^3$ is hydrogen or lower alkyl. More preferably, $R^3$ is hydrogen or alkyl having 1 to 4 carbon atoms, more preferably 1 or 2 carbon atoms. Still more preferably, $R^3$ is hydrogen.

$R^4$ is preferably selected from the group consisting of alkyl, substituted alkyl and cycloalkyl. More preferably, $R^4$ is alkyl having 3 to 6 carbon atoms or cycloalkyl having 5 to 6 carbon atoms. Particularly preferred $R^4$ groups include methyl, n-propyl, isopropyl, 1-hydroxy-2-methylprop-2-yl, n-butyl, tert-butyl, 3-thiomethylpropyl, 3-(thiomethoxy)but-1-yl, cyclohexyl, 4-trifluoromethybenzyl and 3,4,5-trimethoxybenzyl.

$R^5$ is preferably selected from the group consisting of alkyl and cycloalkyl. More preferably, $R^5$ is lower alkyl. Particularly preferred $R^5$ groups include methyl, ethyl, n-propyl, isopropyl and n-butyl.

$R^6$ is preferably selected from the group consisting of alkyl and alkoxycarbonylalkyl (i.e., ROC(O)-alkyl-, where R is alkyl or cycloalkyl). Particularly preferred $R^6$ groups include ethyl, n-propyl, isopropyl, n-butyl, ethoxycarbonylmethyl and 2-(ethoxycarbonyl)ethyl. $R^7$ is preferably hydrogen.

Preferably, $R^8$ is alkyl or alkoxyalkyl (i.e., RO-alkyl-, where R is alkyl). Particularly preferred $R^8$ groups include methyl and methoxyethyl. $R^9$ is preferably hydrogen.

Preferably, X is oxygen.

Preferably, $R^{10}$, $R^{11}$ and $R^{12}$ are independently lower alkyl. More preferably, $R^{10}$, $R^{11}$ and $R^{12}$ are methyl.

W is preferably oxygen.

In one preferred embodiment, this method employs a compound of formula IA:

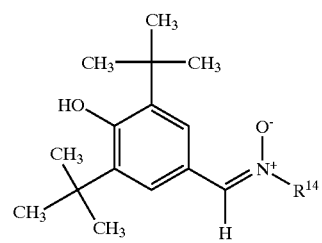

wherein $R^{14}$ is selected from the group consisting of alkyl, substituted alkyl, cycloalkyl and substituted cycloalkyl; and pharmaceutically-acceptable salts thereof and $R^{14}$ is preferably selected from the group consisting of alkyl, substituted alkyl and cycloalkyl. More preferably, $R^{14}$ is alkyl having 3 to 8 carbon atoms or cycloalkyl having 5 to 6 carbon atoms. Particularly preferred $R^{14}$ groups include methyl, n-propyl, isopropyl, 1-hydroxy-2-methylprop-2-yl, n-butyl, tert-butyl, tert-octyl and cyclohexyl.

In another preferred embodiment, this method employs a compound of formula II:

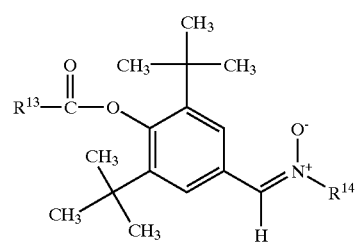

wherein $R^{13}$ is selected from the group consisting of alkyl, substituted alkyl, cycloalkyl and substituted cycloalkyl; and $R^{14}$ is selected from the group consisting of alkyl, substituted alkyl, cycloalkyl and substituted cycloalkyl; and pharmaceutically-acceptable salts thereof.

Preferably, $R^{13}$ is lower alkyl.

$R^{14}$ is preferably selected from the group consisting of alkyl, substituted alkyl and cycloalkyl. More preferably, $R^{14}$ is alkyl having 3 to 6 carbon atoms or cycloalkyl having 5 to 6 carbon atoms. Particularly preferred $R^{14}$ groups include methyl, n-propyl, isopropyl, 1-hydroxy-2-methylprop-2-yl, n-butyl, tert-butyl, 3-thiomethylpropyl, 3-(thiomethoxy)but- 1-yl, cyclohexyl, 4-trifluoromethybenzyl and 3,4,5-trimethoxybenzyl.

In another preferred embodiment, this invention employs a compound of formula III to treat pain:

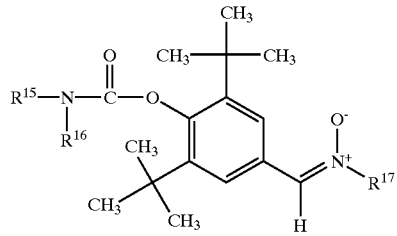

III wherein $R^{15}$ and $R^{16}$ are independently selected from the group consisting of hydrogen, alkyl, substituted alkyl, cycloalkyl, substituted cycloalkyl; or $R^{15}$ and $R^{16}$ can be joined to form an alkylene or substituted alkylene group having from 2 to 10 carbon atoms;

$R^{17}$ is selected from the group consisting of alkyl, substituted alkyl, cycloalkyl and substituted cycloalkyl; and pharmaceutically-acceptable salts thereof.

$R^{15}$ is preferably selected from the group consisting of alkyl and alkoxycarbonylalkyl (i.e., ROC(O)-alkyl-, where R is alkyl or cycloalkyl). Particularly preferred $R^{15}$ groups include ethyl, n-propyl, isopropyl, n-butyl, ethoxycarbonylmethyl and 2-(ethoxycarbonyl)ethyl. $R^{16}$ is preferably hydrogen.

$R^{17}$ is preferably selected from the group consisting of alkyl, substituted alkyl and cycloalkyl. More preferably, $R^{17}$ is alkyl having 3 to 6 carbon atoms or cycloalkyl having 5 to 6 carbon atoms. Particularly preferred $R^{17}$ groups include methyl, n-propyl, isopropyl, 1-hydroxy-2-methylprop-2-yl, n-butyl, tert-butyl, 3-thiomethylpropyl, 3-(thiomethoxy)but-1-yl, cyclohexyl, 4-trifluoromethybenzyl and 3,4,5-trimethoxybenzyl.

In still another preferred embodiment, this invention is directed to the use of a compound of formula IV to treat pain:

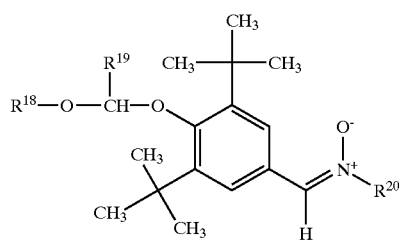

IV wherein $R^{18}$ is selected from the group consisting of alkyl, substituted alkyl, cycloalkyl and substituted cycloalkyl;

$R^{19}$ is selected from the group consisting of hydrogen, alkyl, substituted alkyl, cycloalkyl and substituted cycloalkyl; or $R^{18}$ and $R^{19}$ can be joined to form an alkylene or substituted alkylene group having from 2 to 10 carbon atoms;

$R^{20}$ is selected from the group consisting of alkyl, substituted alkyl, cycloalkyl and substituted cycloalkyl; and pharmaceutically-acceptable salts thereof.

Preferably, $R^{18}$ is alkyl or alkoxyalkyl (i.e., RO-alkyl-, where R is alkyl). Particularly preferred $R^{18}$ groups include methyl and methoxyethyl. $R^{19}$ is preferably hydrogen.

Particularly preferred 3,4,5-trisubstituted aryl nitrone compounds for use in the invention include those having the formulae shown in Tables I, II, III and IV.

TABLE I

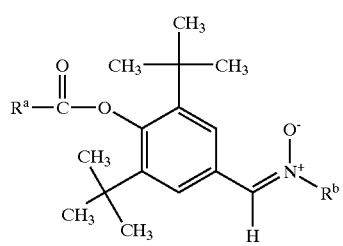

| Number | $R^a$ | $R^b$ |
|---|---|---|
| 1 | $CH_3$— | —$C(CH_3)_3$ |
| 2 | $(CH_3)_2CH$— | —$C(CH_3)_3$ |
| 3 | $CH_3CH_2CH_2$— | —$C(CH_3)_3$ |
| 4 | $CH_3$— | —$CH(CH_3)_2$ |
| 5 | $CH_3$— | —$C(CH_3)_2CH_2OH$ |
| 6 | $CH_3CH_2CH_2CH_2$— | —$C(CH_3)_3$ |
| 7 | $CH_3$— | 4-$CF_3$—Ph— |
| 8 | $CH_3CH_2$— | —$C(CH_3)_3$ |
| 9 | $CH_3$— | —$CH_3$ |
| 10 | $CH_3$— | 3,4,5-tri$(CH_3O$—$)$Ph— |

TABLE II

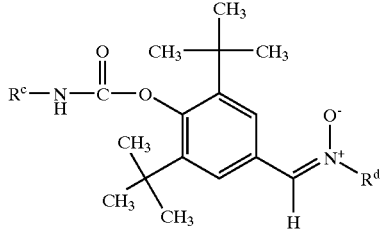

| Number | $R^c$ | $R^d$ |
|---|---|---|
| 11 | $CH_3CH_2$— | —$C(CH_3)_3$ |
| 12 | $CH_3CH_2CH_2$— | —$C(CH_3)_3$ |
| 13 | $CH_3CH_2CH_2CH_2$— | —$C(CH_3)_3$ |
| 14 | $CH_3CH_2OC(O)CH_2CH_2$— | —$C(CH_3)_3$ |
| 15 | $CH_3CH_2OC(O)CH_2$— | —$C(CH_3)_3$ |

TABLE III

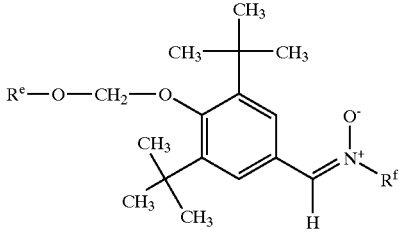

| Number | $R^e$ | $R^f$ |
|---|---|---|
| 16 | $CH_3$— | —$C(CH_3)_3$ |
| 17 | $CH_3$—O—$CH_2CH_2$— | —$C(CH_3)_3$ |
| 18 | $CH_3$— | —$CH_2CH_2CH(SCH_3)CH_3$ |
| 19 | $CH_3$— | —$CH_2CH_2CHSCH_3$ |
| 29 | $CH_3$— | —$CH_2$-(cyclohexyl) |

TABLE III-continued

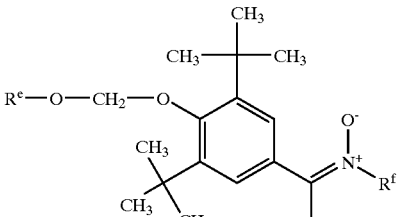

| Number | R$^e$ | R$^f$ |
|---|---|---|
| 30 | CH$_3$— | —CH$_2$-(2-tetrahydrofuryl) |
| 31 | CH$_3$— | -benzyl |

TABLE IV

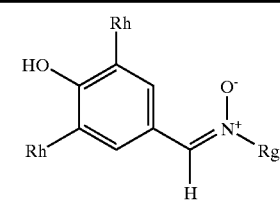

| Number | R$^g$ | R$^h$ |
|---|---|---|
| 20 | —C(CH$_3$)$_3$ | —C(CH$_3$)$_3$ |
| 21 | —C—(CH$_3$)$_2$—CH$_2$—C(CH$_3$)$_3$ | —C(CH$_3$)$_3$ |
| 22 | —C(CH$_3$)$_3$ | —OCH$_3$ |
| 23 | —C—(CH$_2$)$_4$—CH$_3$ | —CH$_3$ |
| 24 | —C(CH$_3$)$_3$ | —CH$_3$ |
| 25 | —C—(CH$_3$)$_2$—CH$_2$OH | —C(CH$_3$)$_3$ |
| 26 | —C—(CH$_3$)$_2$—CH$_2$CH$_3$ | —C(CH$_3$)$_3$ |
| 27 | —CH(CH$_3$)—CH$_3$ | —C(CH$_3$)$_3$ |
| 28 | —CH$_2$Ph | —C(CH$_3$)$_3$ |

TABLE V

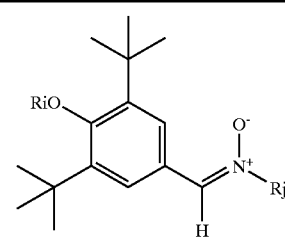

| Number | R$^i$ | R$^j$ |
|---|---|---|
| 32 | —CH$_3$ | —C(CH$_3$)$_3$ |
| 33 | CH$_2$CH$_3$ | —C(CH$_3$)$_3$ |
| 34 | —CH$_2$CO$_2$CH$_2$CH$_3$ | —C(CH$_3$)$_3$ |

Accordingly, in another of its composition aspects, this invention is directed to the use of each of the following individual compounds to treat pain:

α-(4-acetoxy-3,5-di-tert-butylphenyl)-N-tert-butylnitrone
α-(4-isobutanoyloxy-3,5-di-tert-butylphenyl)-N-tert-butylnitrone
α-(4-n-butanoyloxy-3,5-di-tert-butylphenyl)-N-tert-butylnitrone
α-(4-acetoxy-3,5-di-tert-butylphenyl)-N-isopropylnitrone
α-(4-acetoxy-3,5-di-tert-butylphenyl)-N-1-hydroxy-2-methylprop-2-ylnitrone
α-(4-n-pentanoyloxy-3,5-di-tert-butylphenyl)-N-tert-butylnitrone
α-(4-acetoxy-3,5-di-tert-butylphenyl)-N-4-trifluoromethylbenzylnitrone
α-(4-propionyloxy-3,5-di-tert-butylphenyl)-N-tert-butylnitrone
α-(4-acetoxy-3,5-di-tert-butylphenyl)-N-methylnitrone
α-(4-acetoxy-3,5-di-tert-butylphenyl)-N-3,4,5-trimethoxybenzylnitrone
α-[4-(ethylaminocarbonyloxy)-3,5-di-tert-butylphenyl]-N-tert-butylnitrone
α-[4-(n-propylaminocarbonyloxy)-3,5-di-tert-butylphenyl]-N-tert-butylnitrone
α-[4-(n-butylaminocarbonyloxy)-3,5-di-tert-butylphenyl]-N-tert-butylnitrone
α-[4-(2-ethoxycarbonyl)ethylaminocarbonyloxy)-3,5-di-tert-butylphenyl]-N-tert-butylnitrone
α-[4-(2-ethoxycarbonyl)methylaminocarbonyloxy)-3,5-di-tert-butylphenyl]-N-tert-butylnitrone
α-(4-methoxymethoxy-3,5-di-tert-butylphenyl)-N-tert-butylnitrone
α-[4-(2-methoxy)ethoxymethoxy-3,5-di-tert-butylphenyl]-N-tert-butylnitrone
α-(4-methoxymethoxy-3,5-di-tert-butylphenyl)-N-3-(thiomethoxy)but-1-ylnitrone
α-(4-hydroxy-3,5-di-tert-butylphenyl)-N-tert-butylnitrone
α-(4-hydroxy-3,5-di-tert-butylphenyl)-N-tert-octylnitrone
α-(4-methoxymethoxy-3,5-di-tert-butylphenyl)-N-3-thiomethoxypropylnitrone
a-(4-hydroxy-3,5-dimethoxyphenyl)-N-tert-butylnitrone (m.p. 185.4° C.)
a-(4-hydroxy-3,5-dimethylphenyl)-N-hexylnitrone (m.p. 128° C.)
a-(4-hydroxy-3,5-dimethylphenyl)-N-tert-butylnitrone (m.p. 197.5–198.3° C.)
a-(4-hydroxy-3,5-di-tert-butylphenyl)-N-(1,1-dimethyl-2-hydroxyethyl)nitrone (m.p. 185–191° C.)
a-(4-hydroxy-3,5-di-tert-butylphenyl)-N-(1,1-dimethylpropyl)nitrone (m.p. 215° C.)
a-(4-hydroxy-3,5-di-tert-butylphenyl)-N-(1-methylethyl)nitrone (m.p. 176° C.)
a-(4-hydroxy-3,5-di-tert-butylphenyl)-N-benzylnitrone (m.p. 123.3° C.)
α-(4-methoxymethoxy-3,5-di-tert-butylphenyl)-N-cyclohexylmethylnitrone
α-(4-methoxymethoxy-3,5-di-tert-butylphenyl)-N-(2-tetrahydrofuryl) nitrone
α-(4-methoxymethoxy-3,5-di-tert-butylphenyl)-N-benzylnitrone
α-(4-methoxy-3,5-di-tert-butylphenyl)-N-tert-butylnitrone
α-(4-ethoxy-3,5-di-tert-butylphenyl)-N-tert-butylnitrone
α-(4-carbethoxymethoxy-3,5-di-tert-butylphenyl)-N-tert-butylnitrone and pharmaceutically acceptable salts thereof.

In composition aspects, this invention is directed to pharmaceutical compositions comprising a pharmaceutically acceptable carrier and an effective neuropathic pain-treating amount of a compound of formula I, II, III or IV above.

BRIEF DESCRIPTION OF THE DRAWINGS

This invention will be described with reference being made to the accompanying drawings in which.

DETAILED DESCRIPTION OF THE INVENTION

Figure 1:
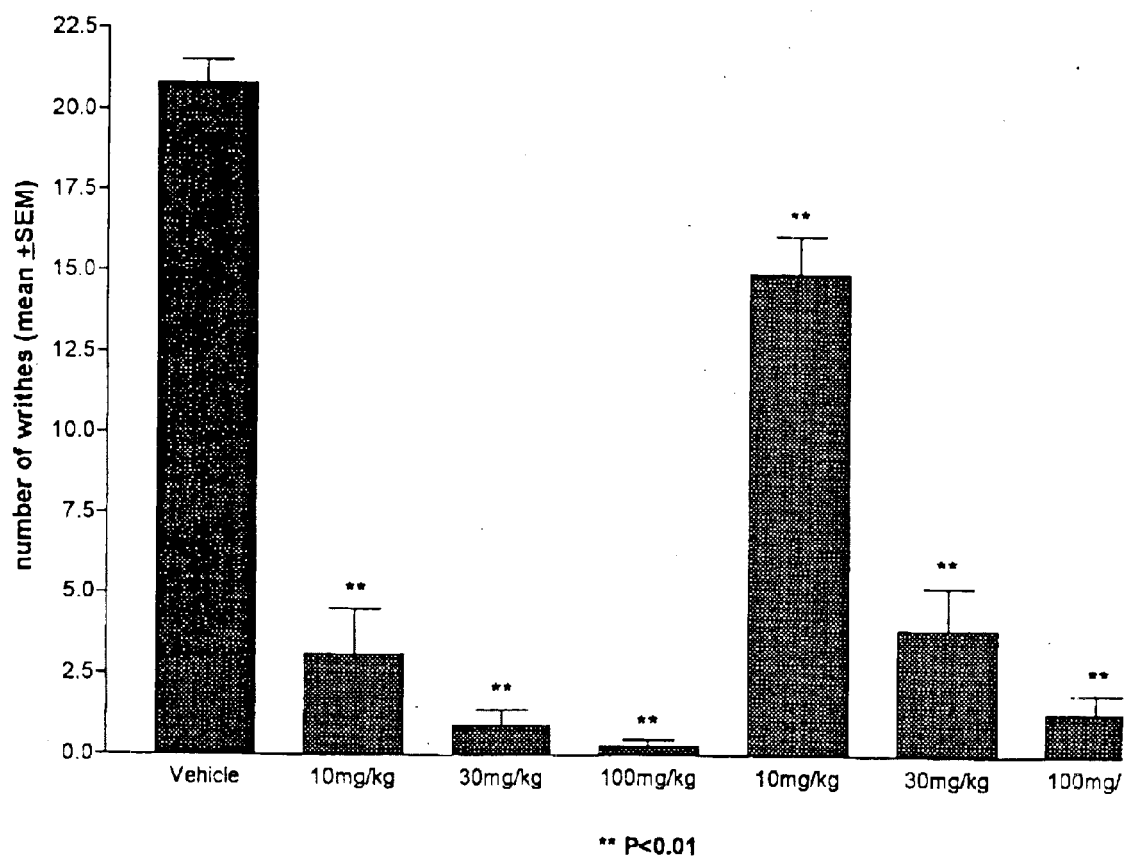
FIG. 1 is a set of bar graphs illustrating the effectiveness of the present invention in an in vivo model for neuropathic pain, the phenylquinone writhing assay.

For the purposes of this invention, the 3,4,5-trisubstituted aryl nitrone compounds are named using conventional nitrone nomenclature, i.e., the carbon atom of the carbon-nitrogen double bond (C=N) is designated the α-position and substituents on the nitrogen atom of the carbon-nitrogen double bond are given the N— prefix.

In some cases, the 3,4,5,-trisubstituted aryl nitrones may contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the 3,4,5-trisubstituted aryl nitrones of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Additionally, all geometric isomers of the nitrone compounds of formula I are included within the scope of this invention including, for example, all isomers (i.e. E and Z isomers) of the carbon-nitrogen double bond of the nitrone functionality.

Definitions

When describing the 3,4,5-trisubstituted aryl nitrones, used in the methods of this invention, the following terms have the following meanings unless otherwise specified.

"Acyl" refers to the group —C(O)R where R is hydrogen, alkyl, aryl or cycloalkyl.

"Acylamino" refers to the group —NRC(O)R where each R is independently hydrogen, alkyl, aryl or cycloalkyl.

"Acyloxy" refers to the group —OC(O)R where R is hydrogen, alkyl, aryl or cycloalkyl.

"Alkenyl" refers to a monvalent branched or unbranched unsaturated hydrocarbon group preferably having from 2 to 10 carbon atoms and more preferably 2 to 6 carbon atoms and having at least 1 and preferably from 1–2 sites of carbon-carbon double bond unsaturation. Preferred alkenyl groups include ethenyl (—CH=$CH_2$), n-propenyl (—$CH_2$CH=$CH_2$), isopropenyl (—C($CH_3$)=$CH_2$), and the like.

"Substituted alkenyl" refers to an alkenyl group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR where R is alkyl. Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" refers to an alkoxy group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonyl" refers to the group —C(O)OR where R is alkyl or cycloalkyl.

"Alkoxycarbonylamino" refers to the group —NRC(O) OR' where R is hydrogen, alkyl, aryl or cycloalkyl, and R' is alkyl or cycloalkyl.

"Alkyl" refers to a monovalent branched or unbranched saturated hydrocarbon group preferably having from 1 to about 10 carbon atoms, more preferably from 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to an alkyl group having from 1 to 6 carbon atoms.

"Substituted alkyl" refers to an alkyl group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkylene" refers to a divalent branched or unbranched saturated hydrocarbon group preferably having from 1 to 10 carbon atoms and more preferably from 1 to 6 carbon atoms. This term is exemplified by groups such as methylene (—$CH_2$—), ethylene (—$CH_2CH_2$—), the propylene isomers (e.g., —$CH_2CH_2CH_2$— and —CH($CH_3$)$CH_2$—) and the like.

"Substituted alkylene" refers to an alkylene group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkynyl" refers to a monovalent branched or unbranched unsaturated hydrocarbon group preferably having from 2 to 10 carbon atoms and more preferably 2 to 6 carbon atoms and having at least 1 and preferably from 1–2 sites of carbon-carbon triple bond unsaturation. Preferred alkynyl groups include ethynyl (—C≡CH), propargyl (—CH$_2$C≡CH) and the like.

"Substituted alkynyl" refers to an alkynyl group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Amino" refers to the group —NH$_2$.

"Substituted amino" refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Aminocarbonyl" refers to the group —C(O)NRR where each R is independently hydrogen, alkyl, aryl and cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted with from 1 to 5 substituents, preferably 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Aryloxy" refers to the group —OR where R is aryl.

"Cycloalkyl" refers to a cyclic alkyl group of from 3 to 10 carbon atoms having a single cyclic ring or multiple condensed or bridged rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple or bridged ring structures such as adamantanyl and the like. The term "lower cycloalkyl" refers to a cycloalkyl group having from 3 to 6 carbon atoms.

"Substituted cycloalkyl" refers to a cycloalkyl group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to a cyclic alkenyl group of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Substituted cycloalkenyl" refers to a cycloalkenyl group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Halo" or "halogen" refers to fluoro, chloro, bromo and iodo. Preferred halo groups are either fluoro or chloro.

"Hydroxyl" refers to the group —OH.

"Keto" or "oxo" refers to the group =O.

"Nitro" refers to the group —NO$_2$.

"Thioalkoxy" refers to the group —SR where R is alkyl.

"Substituted thioalkoxy" refers to a thioalkoxy group having from 1 to 5 substituents, and preferably from 1 to 3 substiutents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Thioaryloxy" refers to the group —SR where R is aryl.

"Thioketo" refers to the group =S.

"Thiol" refers to the group —SH.

"Pharmaceutically-acceptable salt" refers to any salt of a compound used in this invention which retains its biological properties and which is not biologically or otherwise undesirable. Such salts may be derived from a variety of organic and inorganic counter-ions well known in the art and include, by way of example illustration, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. The term "pharmaceutically-acceptable cation" refers to a pharmaceutically acceptable cationic counter-ion of an acidic functional group. Such cations are exemplified by sodium, potassium, calcium, magnesium, ammonium, tetraalkylammonium cations, and the like.

General Synthetic Procedures

The 3,4,5-trisubstituted aryl nitrones used in this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, New York, 1991, and references cited therein.

In a preferred method of synthesis, the 3,4,5-trisubstituted aryl nitrones are prepared by coupling an aryl carbonyl compound of formula V:

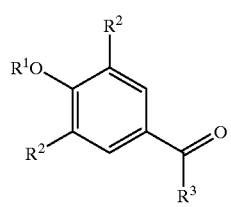

V wherein $R^1$, $R^2$ and $R^3$ are as defined above, with a hydroxylamine of formula VI:

  VI

HO—NH—$R^4$ wherein $R^4$ is as defined above, under conventional reaction conditions.

This coupling reaction is typically conducted by contacting the aryl carbonyl compound V with at least one equivalent, preferably about 1.1 to about 2 equivalents, of hydroxylamine VI in an inert polar solvent such as methanol, ethanol, 1,4-dioxane, tetrahydrofuran, dimethyl sulfoxide, dimethylformamide and the like. This reaction is preferably conducted at a temperature of from about 0° C. to about 100° C. for about 1 to about 48 hours. Optionally, a catalytic amount of an acid, such as hydrochloric acid, acetic acid, p-toluenesulfonic acid, silica gel and the like, may be employed in this reaction. When $R^1$ in formula V is —C(O)$R^3$, at least two equivalents of hydroxylamine VI are employed in this coupling reaction. Upon completion of the reaction, the 3,4,5-trisubstituted aryl nitrone of formula I is recovered by conventional methods including precipitation, chromatographic separation, filtration, distillation, sublimation, and the like.

The aryl carbonyl compounds of formula V employed in the above-described coupling reaction are either known compounds or compounds that can be prepared from known compounds by conventional procedures. For example, aryl carbonyl compounds of formula V where $R^1$ is —C(O)$R^5$ are readily prepared by acylation of the corresponding 4-hydroxy derivative. For example, in a preferred embodiment, 3,5-di-tert-butyl-4-hydroxybenzaldehyde (available from Aldrich Chemical Co., 1001 W. St. Paul Avenue, Milwaukee, Wis., USA 53233–2641) is acetylated by contacting the benzaldehyde with excess acetic anhydride in the presence of an acid catalyst, such as perchloric acid, followed by hydrolysis of the intermediate acetal, to afford 4-acetoxy-3,5-di-tert-butylbenzaldehyde. Other carboxylic anhydrides may also be employed in this reaction including, by way of example, propionic anhydride, butyric anhydride, isobutyric anhydride and the like. Alternatively, such compounds can be prepared by acylation of the 4-hydroxy compound with other acylating agents, such as acyl halides, under conventional reaction conditions. The acyl halides employed in this reaction are preferably acyl chlorides or acyl bromides, such as acetyl chloride, acetyl bromide, propionyl chloride, n-butyryl chloride, isobutyryl chloride and the like. Typically, this reaction is conducted in the presence of a trialkylamine, such as triethylamine, to neutralize the acid generated during the reaction.

Similarly, the aryl carbonyl compounds of formula V where $R^1$ is —C(O)NR$^6$R$^7$ are readily prepared by reaction of the corresponding 4-hydroxy derivative with an isocyanate (i.e., R$^6$R$^7$N=C=O). For example, in a preferred embodiment, 3,5-di-tert-butyl-4-hydroxybenzaldehyde is reacted with ethylisocyanate to afford 4-(ethylaminocarbonyloxy)-3,5-di-tert-butylbenzaldehyde. Typically, this reaction is conducted at ambient temperature in an inert diluent, such as N,N-dimethylformamide, in the presence of an excess of a trialkylamine, such as triethylamine and the like. Other isocyantes may be employed in this reaction including, by way of illustration, n-propylisocyanate, n-butylisocyanate and the like.

Additionally, the aryl carbonyl compounds of formula V where $R^1$ is —CHR$^9$—X—R$^8$ are readily prepared by reacting the corresponding 4-hydroxy derivative with a compound of the formula L—CHR$^9$—X—R$^8$, where L is a leaving group, such as a halogen or a sulfonate ester, and R$^8$, R$^9$ and X are as defined herein. Typically, this reaction is conducted by contacting the 4-hydroxy derivative with an excess of the alkylating agent in the presence of an equimolar amount of a trialkylamine, such as N,N-diisopropylethylamine, in an inert diluent such as 1,2-dichloroethane. Preferred alkylating agents for use in this reaction include, by way of example, methoxymethyl chloride and 2-methoxyethoxymethyl (MEM) chloride.

The hydroxylamine compounds of formula VI above are also known compounds or compounds which can be prepared from known compounds by conventional procedures. Typically, the hydroxylamine compounds of formula VI are prepared by reducing the corresponding nitro compound (i.e., R$^4$—NO$_2$, wherein R$^4$ is as defined above) using a suitable reducing agent such as activated zinc/acetic acid, activated zinc/ammonium chloride or an aluminum/mercury amalgam. This reaction is typically conducted at a temperature ranging from about 15° C. to about 100° C. for about 0.5 to 12 hours, preferably about 2 to 6 hours, in an aqueous reaction media, such as an alcohol/water mixture in the case of the zinc reagents or an ether/water mixture in the case of the aluminum amalgams. Aliphatic nitro compounds (in the form of their salts) can also be reduced to hydroxylamines using borane in tetrahydrofuran. Since some hydroxylamines have limited stability, such compounds are generally prepared immediately prior to reaction with the aryl carbonyl compound of formula V.

Preferred hydroxylamines include, but are not limited to, N-isopropylhydroxylamine, N-n-propylhydroxylamine, N-n-butylhydroxylamine, N-tert-butylhydroxylamine, N-cyclohexylhydroxylamine and the like.

Pharmaceutical Compositions

When employed as pharmaceuticals in the treatment of neuropathic pain, the 3,4,5-trisubstituted aryl nitrones of this invention are administered in the form of a pharmaceutical composition. Such compositions can be prepared using procedures well known in the pharmaceutical art and comprise at least one active compound.

The compounds of this invention are administered in a pharmaceutically effective neuropathic pain-treating amount. The amount of the compound actually administered will typically be determined by a physician, in the light of the relevant circumstances, including the type of pain to be treated, the chosen route of administration, the actual compound administered, the age, weight, and response of the individual patient, the severity of the patient's symptoms, and the like.

The pharmaceutical compositions can be administered by any suitable routes including, by way of illustration, oral, transdermal, subcutaneous, intramuscular, and the like. Depending on the intended route of delivery, the compounds of this invention are preferably formulated as either oral, transdermal or intramuscular injectable compositions.

Pharmaceutical compositions for oral administration can take the form of bulk liquid solutions or suspensions, or bulk powders. More commonly, however, such compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the nitrone compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Transdermal compositions are typically formulated as a topical ointment or cream containing the active ingredient (s), generally in an amount ranging from about 0.01 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example, an oil-in-water cream base. Such topical formulations are well-known in the art and generally include additional ingredients to enhance the dermal penetration or stability of the active ingredients or the formulation. The use of all such known topical formulations and ingredients are included within the scope of this invention.

The compounds can also be administered by a transdermal device. Accordingly, topical administration can be accomplished using a patch either of the reservoir or porous membrane type or of a solid matrix variety.

Injectable compositions are typically based upon injectable sterile saline or phosphate-buffered saline or other injectable carriers known in the art. As before, the 3,4,5-trisubstituted aryl nitrone compound in such compositions is typically a minor component, often being from about 0.05 to 10% by weight with the remainder being the injectable carrier and the like.

The above-described components for orally and topically administrable or injectable compositions are merely representative. Other materials as well as processing techniques and the like are set forth in Part 8 of *Remington's Pharmaceutical Sciences*, 18th edition, 1990, Mack Publishing Company, Easton, Pa., 18042, which is incorporated herein by reference.

The following formulation examples illustrate representative pharmaceutical compositions for use in this invention. The present invention, however, is not limited to the use of the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240–270 mg tablets (80–90 mg of active nitrone compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active nitrone compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Injection

The compound of formula I is dissolved in a buffered sterile saline injectable aqueous medium to a concentration of approximately 5 mg/mL.

Formulation 5—Ointment

Stearyl alcohol (250 g) and white petrolatum (250 g) are melted at about 75° C. and then a mixture of a compound of formula I (50 g), methylparaben (0.25 g), propylparaben (0.15 g), sodium lauryl sulfate (10 g), and propylene glycol (120 g) dissolved in water (about 370 g) is added and the resulting mixture is stirred until it congeals.

Compound Utility

The 3,4,5-trisubstituted aryl nitrones have now been discovered to provide analgesia against neuropatic pain. Accordingly, these compounds and pharmaceutical compositions find use as therapeutics for treating neuropathic pain in mammals including humans.

As discussed above, the compounds described herein are suitable for use in a variety of drug delivery systems. Injection dose levels for treating pain related conditions range from about 0.1 mg/kg/hour to at least 10 mg/kg/hour, all for from about 1 to about 120 hours and especially 24 to 96 hours by an intravenous route. An intramuscular injection regimen should deliver the amount in one to three daily doses. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the treatment of long-term conditions, such as chronic neuropathic pain, the regimen for treatment may stretch over many months or years so oral dosing is preferred for patient convenience and tolerance. With oral dosing, one to five and especially two to four and typically three oral doses per day are representative regimens. Using these dosing patterns, each dose provides from about 0.1 to about 20 mg/kg of the nitrone, with preferred doses each providing from about 0.1 to about 10 mg/kg and especially about 1 to about 5 mg/kg.

The nitrone compounds can be administered as the sole active agent or they can be administered in combination with other active analgesic agents, such as opioid analgesic agents.

The following synthetic and biological examples are offered to illustrate the synthesis of compounds used in this invention and the testing of the pain treatment. They are not to be construed in any way as limiting the scope of this invention.

EXAMPLES

In the examples below, the following abbreviations have the following meanings. Abbreviations not defined below have their generally accepted meaning.

| | |
|---|---|
| bd = | broad doublet |
| bs = | broad singlet |
| d = | doublet |
| dd = | doublet of doublets |
| dec = | decomposed |
| dH$_2$O = | distilled water |
| ELISA = | enzyme-linked immuno-sorbent assay |
| EtOAc = | ethyl acetate |
| EtOH = | ethanol |
| g = | grams |
| h = | hours |
| Hz = | hertz |
| ip = | intraperitoneal |
| L = | liter |
| m = | multiplet |
| min = | minutes |
| M = | molar |
| MeOH = | methanol |
| mg = | milligram |
| MHz = | megahertz |
| mL = | milliliter |
| mmol = | millimole |
| m.p. = | melting point |
| N = | normal |
| po = | per os, oral |
| q = | quartet |
| quint. = | quintet |
| s = | singlet |
| t = | triplet |
| THF = | tetrahydrofuran |
| tlc = | thin layer chromatography |
| µg = | microgram |
| µL = | microliter |
| UV = | ultraviolet |

In the examples below, all temperatures are in degrees Celsius (unless otherwise indicated). Example A-N describe the synthesis of intermediates useful for preparing nitrones of this invention; Examples 1–19 describe the synthesis of various nitrones; and Examples I-VI describe the testing of such compounds.

Example A

Synthesis of N-tert-Butylhydroxylamine

Zinc dust (648 g) was added in portions to a cooled mixture of 2-methyl-2-nitropropane (503 g) and ammonium chloride (207 g) in deionized water (6 L) at such a rate so as to maintain the temperature below 18° C. The reaction mixture was stirred mechanically for 15 hours and then filtered. The solid was washed with hot water (1.75 L). The combined filtrate was saturated with potassium carbonate (4.6 Kg) and extracted with ethyl acetate (2×1300 mL). The organic solution was dried over anhydrous sodium sulfate, filtered and rotary evaporated to give the title compound (329 g, 75.7% yield) as white crystals. This material was used without further purification.

Spectroscopic data were as follows:

$^1$H NMR (CDCl$_3$, 270 MHz) δ=1.090 (s, 3CH$_3$).

Example B

Synthesis of N-Isopropylhydroxylamine

Using the procedure of Example A above and 2-nitropropane, the title compound was prepared. The crude hydroxylamine product was used without further purification.

Example C

Synthesis of N-Cyclohexylhydroxylamine

Using the procedure of Example A above and nitrocyclohexane, the title compound can be prepared. Alternatively, N-cyclohexylhydroxylamine hydrochloride may be purchased commercially from Aldrich Chemical Company, Inc., Milwaukee, Wis. USA and neutralized with a base, such as potassium carbonate, to provide the title compound.

Example D

Synthesis of 4-Acetoxy-3,5-di-tert-butylbenzaldehyde 3,5-Di-tert-butyl-4-hydroxybenzaldehyde (100 g, 0.411 moles) was placed in a 5 L round-bottomed flask equipped with a mechanical stirrer. Acetic anhydride (300 mL) was added with stirring followed by 70% perchloric acid (0.600 mL). The solid immediate dissolved and a blue colored solution formed. The reaction mixture was stirred overnight under nitrogen. The reactions progress was determined by TLC. After completion of the reaction, the flask was cooled in an ice bath. While stirring the reaction mixture vigorously, ice water was added in small portions. The flask became warm during addition of the water. A total of 2 L of water was added. An oil separated and upon continuous stirring the oil solidified to provide brown lumps. The brown lumps were separated in a Buchner funnel and the solid was washed freely with water to remove acetic acid. The solid was then dried under vacuum.

To a solution of the solid in ethanol (250 mL) was added concentrated hydrochloric acid (25 mL). The resulting solution was boiled for ten minutes and then left to cool. While stirring, the reaction mixture was poured into 2 L of water and an oil separated. Upon continuous stirring, the oil solidified to form brown lumps. The solid was separated and packed in Buchner funnel and washed freely with water (about one liter). The solid was then dried on a mechanical pump to afford the title compound in 99.4% yield as a light brown solid, m.p. 65.2–74.5° C.

Spectroscopic data were as follows:

$^1$H NMR (CDCl$_3$, 270 MHz): δ=9.96 (1H, s, carbonyl H), 7.86 (2H, s, phenyl H), 2.38 (3H, s, 3CH$_3$), 1.39 (18H, s, 18CH$_3$).

Example E

Synthesis of 4-Isobutanoyl-3,5-di-tert-butylbenzaldehyde 3,5-Di-tert-butyl-4-hydroxybenzaldehyde (10 g, 0.041 mol) was placed in a 500-mL round-bottomed flask fitted with a mechanical stirrer. Isobutyric anhydride (40 mL) was added with stirring, followed by 0.200 mL of 40% perchloric acid. The solid immediately dissolved to form a red color solution. The reaction mixture was stirred overnight under nitrogen. The reaction progress was determined by TLC. After completion of reaction, the reaction mixture was cooled in an ice bath and added to 400 mL of vigorously stirred ice water. The mixture became warm and an oil separated. The oil was extracted with methylene chloride and the organic layer was washed with 1.5M NaOH solution (2×100 mL), water (2×100 mL) and then dried over magnesium sulfate. The solvent was removed in vacuo to afford a red oil.

To a solution of the red oil in ethanol (200 mL) was added concentrated hydrochloric acid (50 mL). The resulting solution was boiled for ten minutes and the solution was left to cool. While stirring, the mixture was then poured into 2 L of water and an oil separated. Upon continuous stirring, the oil solidified to brown lumps. The solid was separated and packed in Buchner funnel and then washed freely with water to remove acetic acid (about one liter). The solid was then dried on a mechanical pump to afford the title compound (56.7% yield) which was used without further purification.

Example F

Synthesis of 4-n-Butanoyl-3,5-di-tert-butylbenzaldehyde 3,5-Di-tert-butyl-4-hydroxybenzaldehyde (15 g, 0.062 mol) was placed in a 500-mL round-bottomed flask fitted with a mechanical stirrer. n-Butyric anhydride (50 mL) was added with stirring, followed by 0.200 mL of 40% perchloric acid. The solid immediately dissolved to form a blue colored solution. The reaction mixture was stirred overnight under nitrogen. The reaction progress was determined by TLC. After completion of reaction, the reaction mixture was cooled in an ice bath and added to 400 mL of vigorously stirred ice water. The mixture became warm and an oil separated. The oil was extracted with methylene chloride and the organic layer was washed with 5% NaOH (4×100 mL), brine (1×100 mL), water (4×100 mL) and dried over MgSO4. The solvent was removed in vacuo to afford a red oil.

To a solution of the red oil in ethanol (200 mL) was added concentrated hydrochloric acid (40 mL). The resulting solution was boiled for ten minutes and left to cool. While stirring, the mixture was then poured into 2 L of water and an oil separated. Upon continuous stirring, the oil did not solidify, so the mixture was extracted with methylene chloride. The organic layer was washed with saturated NaHCO$_3$ (2×100 mL), water (3×100 mL) and dried over MgSO$_4$. The solvent was removed in vacuo to afford the title compound as a red oil (77.6% yield) which was used without further purification.

Example G

Synthesis of 4-n-Pentanoyl-3,5-di-tert-butylbenzaldehyde 3,5-Di-tert-butyl-4-hydroxybenzaldehyde (10.0 g, 0.0.081 mol) was placed in a 500-mL round-bottomed flask fitted with a mechanical stirrer. Valeric anhydride (50 mL) was added with stirring, followed by 0.200 mL of 40% perchloric acid. The solid immediately dissolved to form a green colored solution. The reaction mixture was stirred overnight under nitrogen. The reaction progress was determined by TLC. After completion of reaction, the reaction mixture was cooled in an ice bath and added to 400 mL of vigorously stirred ice water. The mixture became warm and an oil separated. The oil was extracted with methylene chloride and the organic layer was washed with 5% NaOH (3×50 mL), brine (3×50 mL), water (3×100 mL) and dried over magnesium sulfate. The solvent was removed in vacuo to afford a thick oil.

To a solution of the oil in ethanol (200 mL) was added concentrated hydrochloric acid (50 mL). The resulting solution was boiled for ten minutes and left to cool. While stirring, the mixture was then poured into 2 L of water and an oil separated. Upon continuous stirring, the oil did not solidify, so the mixture was extracted with methylene chloride. The organic layer was washed with saturated NaHCO$_3$ (3×50 mL), water (5×100 mL) and dried over MgSO$_4$. The solvent was removed in vacuo to afford the title compound as a red oil which was used without further purification.

Example H

Synthesis of 4-(Ethylaminocarbonyloxy)-3,5-di-tert-butylbenzaldehyde

To a solution of 3,5-di-tert-butyl-4-hydroxybenzaldehyde (5 g, 20 mmol) in DMF (100 mL) was added triethylamine (3.5 mL, 25 mmol) and the solution was stirred for 15 min at room temperature. Ethyl isocyanate (1.95 mL, 25 mmol) was added and the reaction mixture was stirred for 2 h at room temperature until no more hydroxybenzaldehyde was detected by TLC (R$_f$=0.78 for product and 0.89 for starting material using 1:1 hexanes/EtOAc). The reaction solution was concentrated by azeotropic removal of DMF with water. The resulting suspension was filtered, washed with water and dried in a vacuum oven to afford 96% of the title compound as a light buff solid.

Spectroscopic data were as follows:

$^1$H NMR (DMSO-d$_6$, 270 MHz): δ=9.96 (1H, s, aldehyde CHO), 8.04 (1H, t, carbamate NH), 7.83 (2H, s, phenyl H), 3.09 (2H, m, ethyl CH$_2$), 1.34 (18H, s, 6CH$_3$), 1.07 (3H, t, ethyl CH$_3$).

$^{13}$C NMR (DMSO-d$_6$, 270 MHz): δ=193.4, 155.1, 154.2, 145.0, 133.3, 127.8, 35.9, 31.4, 30.5.

Example I

Synthesis of 4-(n-Propylaminocarbonyloxy)-3,5-di-tert-butylbenzaldehyde

The title compound was prepared in DMF using 3,5-di-tert-butyl-4-hydroxybenzaldehyde and n-propyl isocyanate according to the procedure described in Example H. The title compound was isolated in 100.0% yield as an off-white solid.

Example J

Synthesis of 4-(n-Butylaminocarbonyloxy)-3,5-di-tert-butylbenzaldehyde

The title compound was prepared in DMF using 3,5-di-tert-butyl-4-hydroxybenzaldehyde and n-butyl isocyanate according to the procedure described in Example H. The title compound was isolated in 87.5% yield as a buff solid.

Example K

Synthesis of 4-(2-Ethoxycarbonyl)ethylaminocarbonyloxy)-3,5-di-tert-butylbenzaldehyde The title compound was prepared in DMF using 3,5-di-tert-butyl-4-hydroxybenzaldehyde and ethyl 3-isocyanatopropionate according to the procedure described in Example H. The title compound was isolated in 100% yield as an off-white solid.

Example L

Synthesis of 4-(2-Ethoxycarbonyl)methylaminocarbonyloxy)-3,5-di-tert-butylbenzaldehyde The title compound was prepared in DMF using 3,5-di-tert-butyl-4-hydroxybenzaldehyde and ethyl 2-isocyanatoacetate according to the procedure described in Example H. The title compound was isolated in 100% yield as an off-white solid.

Example M

Synthesis of 4-Methoxymethoxy-3,5-di-tert-butylbenzaldehyde

To a solution of 3,5-di-tert-butyl-4-hydroxybenzaldehyde (10 g, 40 mmol) in 1,2-dichloroethane (200 mL) was added N,N-diisopropylethylamine (6.97 mL, 40 mmol) and the solution was stirred for 1 h at room temperature. Chloromethoxymethyl ether (3.77 mL, 50 mmol) was added and the reaction mixture was stirred for 1 h at room temperature and then refluxed for 16 h until no more hydroxybenzaldehyde was detected by TLC ($R_f$=0.78 for product and 0.70 for starting material using 1:1 hexanes/EtOAc). The reaction mixture was cooled to room temperature and washed with water. The organic layer was concentrated and the residue applied to a silica gel column and eluted with mixture of pentane/EtOAc. The title compound was isolated in 100% yield as a brown oil.

Spectroscopic data were as follows:

$^1$H NMR (DMSO-$d_6$, 270 MHz): δ=9.89 (1H, s, aldehyde CHO), 7.80 (2H, s, phenyl H), 4.92 (2H, s, CH$_2$), 3.64 (3H, s, CH$_3$), 1.46 (18H, s, 6CH$_3$).

$^{13}$C NMR (DMSO-$d_6$, 270 MHz): δ=192.11, 160.11, 145.77, 131.65, 128.55, 100.98, 57.66, 35.99 and 30.16.

Example N

Synthesis of 4-(2-Methoxy)ethoxymethoxy-3,5-di-tert-butylbenzaldehyde

To a solution of 3,5-di-tert-butyl-4-hydroxybenzaldehyde (8 g, 33 mmol) in 1,2-dichloroethane (150 mL) was added N,N-diisopropylethylamine (6.97 mL, 40 mmol) and the solution was stirred for 1 h at room temperature. 2-Methoxyethoxymethyl (MEM) chloride (5.7 mL, 50 mmol) was added and the reaction mixture was stirred for 1 h at room temperature and then at reflux for 26 h until no more hydroxybenzaldehyde was detected by TLC ($R_f$=0.92 for product and 0.70 for starting material using 1:1 hexanes/EtOAc). The reaction mixture was cooled to room temperature and washed with water. The organic layer was concentrated and the residue applied to a silica gel column and eluted with mixture of pentane/EtOAc. The title compound was isolated (98% yield) as a brown oil.

Example 1

Synthesis of α-(4-Acetoxy-3,5-di-tert-butylphenyl)-N-tert-butylnitrone

4-Acetoxy-3,5-di-tert-butylbenzaldehyde (113.16 g, 0.41 mol) was placed in a 2 L round-bottomed flask fitted with a magnetic stirrer. Benzene (500 mL) was added and the mixture was stirred until the solids dissolved. To the resulting red solution was added tert-butylhydroxylamine (43.80 g, 0.49 mol) and silica gel (20 g). The mixture was refluxed overnight at which time TLC showed no remaining starting material ($R_f$=0.31 for product and 0.80 for starting material using 3:1 hexanes/EtOAc). The benzene was removed in vacuo on a rotovap to provide a grey solid. The solid was dissolved in a minimum amount of ethyl acetate and the flask was left to stand in the freezer. The white crystals which formed were separated, washed with hexanes and dried under vacuum to afford 105.78 g of the title compound as a crystalline white solid (74.4% yield), m.p. 227.0–248.9° C.

Spectroscopic data were as follows:

$^1$H NMR (CDCl$_3$, 270 MHz): δ=8.32 (1H, s, phenyl H), 7.50 (1H, s, nitronyl H). 2.35 (3H, s, 1CH$_3$), 1.61 (9H, s, 3CH$_3$), 1.37, s, 18 CH$_3$).

$^{13}$C NMR (CDCl$_3$, 270 MHz): δ=170.7, 149.2, 142.6, 129.7, 128.4, 127.2, 70.7, 35.5, 31.4, 28.5, 22.6.

Example 2

Synthesis of α-(4-Isobutanoyl-3,5-di-tert-butylphenyl)-N-tert-butylnitrone

To a solution of 4-isobutanoyl-3,5-di-tert-butylbenzaldehyde (7.00 g, 0.023 mol) in benzene (200 mL) was added tert-butylhydroxylamine (2.56 g, 0.029 mol) and p-toluenesulfonic acid (0.100 g). Using a Dean-Stark trap, the resulting mixture was refluxed until no more aldehyde was detected by TLC ($R_f$=0.30 for product and 0.89 for starting material using 3:1 hexanes/EtOAc). The solvent was removed in vacuo and the residue was thoroughly washed with hexanes. The title compound was isolated in 50.8% yield as a white solid, m.p. 197.1–208.1° C.

Spectroscopic data were as follows:

$^1$H NMR (CDCl$_3$, 270 MHz): δ=8.32 (2H, s, phenyl), 7.51 (1H, s, nitronyl H), 2.87 (1H, q, J=7.17 Hz, isobutyryl H), 1.61 (9H, s, 9CH$_3$), 1.38 (6H, d, J=7.17, 6CH$_3$), 1.36 (18H, s, 18CH$_3$).

¹³C NMR (CDCl$_3$, 270 MHz): δ=176.0, 150.2, 142.7, 129.9, 128.1, 127.1, 70.7, 35.5, 35.2, 31.3, 28.5, 18.7.

Example 3

Synthesis of α-(4-n-Butanoyl-3,5-di-tert-butylphenyl)-N-tert-butylnitrone

To a solution of 4-n-butanoyl-3,5-di-tert-butylbenzaldehyde (9.63 g, 0.032 mol) in benzene (200 mL) was added tert-butylhydroxylamine (3.52 g, 0.040 mol) and p-toluenesulfonic acid (0.100 g). Using a Dean-Stark trap, the resulting solution was refluxed until no more aldehyde was detected by TLC (R$_f$=0.30 for product and 0.91 for starting material using 3:1 hexanes/EtOAc). The solvent was removed in vacuo and the residue was crystallized from EtOAc and hexanes to afford the titled compound (50.2% yield) as a white solid, m.p. 216.9–236.5° C.

Spectroscopic data were as follows:

¹H NMR (CDCl$_3$, 270 MHz): δ=8.32 (2H, s, phenyl H), 7.50 (1H, s, nitronyl H), 2.61 (2H, t, J=7.67 Hz, 2CH$_2$), 1.78 (2H, m, J=4.70 Hz, 2CH$_2$), 1.61 (9H, s, 9CH$_3$), 1.36 (18H, s, 18CH$_3$), 1.05 (3H, t, J=7.42 Hz, 3CH$_3$).

¹³C NMR (CDCl$_3$, 270 MHz): δ=173.2, 149.5, 142.7, 129.8, 128.2, 127.1, 70.7, 37.6, 35.5, 31.4, 28.5, 17.7, 13.8.

Example 4

Synthesis of α-(4-Acetoxy-3,5-di-tert-butylphenyl)-N-isobutylnitrone

To a solution of 4-acetoxy-3,5-di-tert-butylbenzaldehyde (17.0 g, 0.0615 mol) in methanol (250 mL) was added isobutylhydroxylamine (5.36 g, 0.0714 mol) and concentrated hydrochloric acid (10 drops). Using a Dean-Stark trap, the resulting solution was refluxed until no more aldehyde was detected by TLC (R$_f$=0.23 for product and 0.84 for starting material using 3:1 hexanes/EtOAc) The solvent was removed in vacuo and the residue was a red oil which when triturated with hexanes it turned into solid. The solid was separated and washed completely with hexanes. The titled compound was isolated in 52.3% yield as a white solid, m.p. 176.8–180.4° C.

Spectroscopic data were as follows:

¹H NMR (CDCl$_3$, 270 MHz): δ=8.3 (2H, s, phenyl H), 7.42 (1H, s, nitronyl H), 4.20 (1H, q, J=6.50 Hz, 1CH), 2.35 (3H, s, 3CH$_3$), 1.50 (6H, d, J=6.43 Hz, 6CH$_3$), 1.37 (18H, s, 18CH$_3$).

¹³C NMR (CDCl$_3$, 270 MHz): δ=170.7, 150.1, 142.7, 131.9, 128.0, 127.0, 67.8, 35.5, 31.3, 22.6, 20.9.

Example 5

Synthesis of α-(4-Acetoxy-3,5-di-tert-butylphenyl)-N-1-hydroxy-2-methylprop-2-ylnitrone To a solution of 4-acetoxy-3,5-di-tert-butylbenzaldehyde (10.0 g, 0.0362 mol) in benzene (200 mL) was added N-(1-hydroxy-2-methylprop-2-yl) hydroxylamine (5.55 g, 0.0543 mol) and p-toluenesulfonic acid (0.090 g). Using a Dean-Stark trap, the resulting mixture was refluxed until no more aldehyde was detected by TLC(R$_f$=0.20 for product and 0.98 for starting material using 1:1 hexanes/EtOAc). The solvent was removed in vacuo and the residue was washed with hot hexanes. The title compound was isolated (83.9% yield) as a off white solid, m.p. 204.3–204.8° C.

Spectroscopic data were as follows:

¹H NMR (CDCl$_3$, 270 MHz): δ=8.30 (2H, s, phenyl H), 7.46 (1H, s, nitronyl H). 3.79 (2H, s, 2CH$_2$), 2.36 (3H, s, 3CH$_3$), 1.60, s, 6CH$_3$), 1.37 (18H, s, 18CH$_3$).

¹³C NMR (CDCl$_3$, 270 MHz): δ=171.1, 150.1, 142.9, 132.3, 127.7, 72.8, 69.8, 35.5, 31.6, 31.3, 23.9, 22.6.

Example 6

Synthesis of α-(4-n-Pentanoyl-3,5-di-tert-butylphenyl)-N-tert-butylnitrone

To a solution of 4-pentanoyl-3,5-di-tert-butylbenzaldehyde (17.48 g, 0.050 mol) in benzene (250 mL) was added tert-butylhydroxylamine (4.57 g, 0.0510 mol) and p-toluenesulfonic acid (0.080 g). Using a Dean-Stark trap, the resulting mixture was refluxed until no more aldehyde was detected by TLC (R$_f$=0.43 for product using 1:1 hexanes/EtOAc). The solvent was removed in vacuo and the residue was thoroughly washed with hexanes. The title compound was isolated (56.50% yield) as a white solid, m.p. 195.5–204.8° C.

Spectroscopic data were as follows:

¹H NMR (CDCl$_3$, 270 MHz): δ=8.31 (2H, s, phenyl H), 7.50 (1H, s, nitronyl H). 2.63 (2H, t, J=7.80 2CH), 1.85–1.67 (2H, m, 2CH$_2$), 1.61 (9H, s, 9CH$_3$), 1.52–1.36 (2H, m, 2CH), 1.36 (18H, s, 18CH$_3$), 0.97 (3H, t, J=7.30, 3CH$_3$).

¹³C NMR (CDCl$_3$, 270 MHz): δ=173.2, 149.4, 142.7, 129.8, 128.2, 127.1, 70.7, 35.5, 35.4, 31.4, 28.4, 26.2, 22.2, 13.8.

Examples 7–10

Using the appropriate starting materials and the procedures described herein, the following additional compounds were prepared:

α-(4-acetoxy-3,5-di-tert-butylphenyl)-N-4-trifluoromethylbenzylnitrone (m.p. 217–232° C.);

α-(4-propionyloxy-3,5-di-tert-butylphenyl)-N-tert-butylnitrone (m.p. 202–222° C.);

α-(4-acetoxy-3,5-di-tert-butylphenyl)-N-methylnitrone (m.p. 136–143° C.); and

α-(4-acetoxy-3,5-di-tert-butylphenyl)-N-3,4,5-trimethoxybenzylnitrone (m.p. 231.7–235° C.).

Example 11

Synthesis of α-[4-(Ethylaminocarbonyloxy-3,5-di-tert-butylphenyl]-N-tert-butylnitrone To a solution of 3,5-di-tert-butyl-4-(ethylaminocarbonyloxy)-benzaldehyde (5 g, 16 mmol) in benzene (200 mL) was added tert-butylhydroxylamine (2.14 g, 24 mmol). The resulting solution was refluxed for 96 h until no more aldehyde was detected by TLC (R$_f$=0.57 for product and 0.78 for starting material using 1:1 hexanes/EtOAc). The solvent was removed in vacuo and the residue applied to a silica gel column and eluted with mixture of hexane/EtOAc. The title compound was isolated in 57% yield as a white solid, m.p. 202.2–212.2° C.

Spectroscopic data were as follows:

¹H NMR (DMSO-d$_6$, 270 MHz): δ=8.37 (2H, s, phenyl H), 7.86 (1H, t, J=6.3 Hz, carbamate NH), 7.83 (1H, s, nitronyl H), 3.08 (2H, quintet, J=6.3 Hz, ethyl CH$_2$), 1.49 (9H, s, 3CH$_3$), 1.31 (18H, s, 6CH$_3$), 1.06 (3H, t, J=6.4 Hz, ethyl CH$_3$).

¹³C NMR (DMSO-d$_6$, 270 MHz): δ=155.8, 149.6, 143.30, 129.5, 128.7, 126.9, 70.6, 35.8, 31.6, 28.5 and 15.7.

Example 12

Synthesis of α-[4-(n-Propylaminocarbonyloxy-3,5-di-tert-butylphenyl]-N-tert-butylnitrone The title compound was prepared in benzene using 3,5-di-tert-butyl-4-(n-propylaminocarbonyloxy)benzaldehyde and tert-butylhydroxylamine according to the procedure described in Example 11. The title compound was isolated in 96.6% yield as a white solid, m.p. 206.5–214.0° C.

Spectroscopic data were as follows:

$^1$H NMR (DMSO-$d_6$, 270 MHz): δ=8.38 (2H, s, phenyl H), 7.90 (1H, t, J=5.8 Hz, carbamate NH), 7.84 (1H, s, nitronyl H), 3.02 (2H, q, J=6.5 Hz, propyl NCH$_2$), 1.50 (9H, s, 3CH$_3$), 1.45 (3H, hextet, J=7.2 Hz, propyl CH$_2$), 1.32 (18H, s, 6CH$_3$), 0.88 (3H, t, J=7.3 Hz, propyl CH$_3$).

$^{13}$C NMR (DMSO-$d_6$, 270 MHz): δ=155.7, 149.7, 143.3, 129.5, 128.7, 127.0, 70.6, 42.8, 35.8, 31.7, 28.5, 23.1 and 11.8.

Example 13

Synthesis of α-[4-(n-Butylaminocarbonyloxy-3,5-di-tert-butylphenyl]-N-tert-butylnitrone The title compound was prepared in benzene using 3,5-di-tert-butyl-4-(n-butylaminocarbonyloxy)benzaldehyde and tert-butylhydroxylamine according to the procedure described in Example 11. The title compound was isolated in 93.4% yield as a white solid, m.p. 203.6–205.1° C.

Spectroscopic data were as follows:

$^1$H NMR (DMSO-$d_6$, 270 MHz): δ=8.38 (2H, s, phenyl H), 7.88 (1H, t, J=5.7 Hz, carbamate NH), 7.84 (1H, s, nitronyl H), 3.05 (2H, q, J=6.3 Hz, n-butyl NCH$_2$), 1.50 (9H, s, 3CH$_3$), 1.45–1.37 (4H, m, n-butyl 2 CH$_2$), 1.31 (18H, s, 6CH$_3$), 0.87 (3H, t, J=7.1 Hz, n-butyl CH$_3$).

$^{13}$C NMR (DMSO-$d_6$, 270 MHz): δ=155.6, 149.7, 143.3, 129.5, 128.7, 127.0, 70.6, 40.7, 35.8, 31.9, 31.6, 28.5, 19.9 and 14.2.

Example 14

Synthesis of α-[4-(2-Ethoxycarbonyl)ethylaminocarbonyloxy-3,5-di-tert-butylphenyl]-N-tert-butylnitrone The title compound was prepared in benzene using 3,5-di-tert-butyl-4-(2-ethoxycarbonyl)ethylaminocarbonyloxy)benzaldehyde and tert-butylhydroxylamine according to the procedure described in Example 11. The title compound was isolated in 88.4% yield as a white solid, m.p. 130.5–146.3° C.

Spectroscopic data were as follows:

$^1$H NMR (DMSO-$d_6$, 270 MHz): δ=8.38 (2H, s, phenyl H), 8.01 (1H, t, J=6.0 Hz, carbamate NH), 7.84 (1H, s, nitronyl H), 4.08 (2H, q, J=7.0 Hz, ethyl OCH$_2$), 3.28 (2H, t, J=6.0 Hz, propionate NCH$_2$), 2.50 (2H, t, J=6.0 Hz, propionate COCH$_2$), 1.49 (9H, s, 3CH$_3$), 1.26 (18H, s, 6 CH$_3$), 1.19 (3H, t, J=7.0 Hz, ethyl CH$_3$). $^{13}$C NMR (DMSO-$d_6$, 270 MHz): δ=171.5, 155.6, 149.5, 143.3, 129.4, 128.8, 127.0, 70.6, 60.5, 37.2, 35.8, 34.6, 31.7, 28.5, and 14.7.

Example 15

Synthesis of α-[4-(2-Ethoxycarbonyl)methylaminocarbonyloxy-3,5-di-tert-butylphenyl]-N-tert-butylnitrone The title compound was prepared in benzene using 3,5-di-tert-butyl-4-(2-ethoxycarbonyl)methylaminocarbonyloxy)benzaldehyde and tert-butylhydroxylamine according to the procedure described in Example 11. The title compound was isolated in 42% yield as a white solid, m.p. 177.2–181.6° C.

Spectroscopic data were as follows:

$^1$H NMR (DMSO-$d_6$, 270 MHz): δ 8.38 (2H, s, phenyl H), 8.35 (1H, t, J=5.7 Hz, carbamate NH), 7.84 (1H, s, nitronyl H), 4.10 (2H, q, J=7.0 Hz, ethyl OCH$_2$), 3.83 (2H, d, J=5.7 Hz, NCH$_2$), 1.50 (9H, s, 3 CH$_3$), 1.32 (18H, s, 6CH$_3$), 1.19 (3H, t, J=7.0 Hz, ethyl CH$_3$).

$^{13}$C NMR (DMSO-$d_6$, 270 MHz): δ=170.3, 155.9, 143.3, 129.4, 128.9, 127.0, 70.7, 61.0, 42.9, 35.8, 31.7, 28.5, and 14.6.

Example 16

Synthesis of α-(4-Methoxymethoxy-3,5-di-tert-butylphenyl)-N-tert-butylnitrone

To a solution of 3,5-di-tert-butyl-4-methoxymethoxybenzaldehyde (11.42 g, 40 mmol) in benzene (200 mL) was added tert-butylhydroxylamine (4.0 g, 50 mmol). The resulting solution was refluxed for 72 h until no more aldehyde was detected by TLC ($R_f$=0.56 for product and 0.78 for starting material in 1:1 hexanes/EtOAc). The solvent was removed in vacuo and the residue was suspended in hexane/EtOAc. The suspension was filtered, washed with hexanes and dried to afford the title compound (69% yield) as a white solid, m.p. 202.2–205.9° C.

Spectroscopic data were as follows:

$^1$H NMR (DMSO-$d_6$, 270 MHz): δ=8.37 (2H, s, phenyl H), 7.79 (1H, s, nitronyl H), 4.84 (2H, s, OCH$_2$), 3.54 (3H, s, OCH$_3$), 1.48 (9H, s, 3CH$_3$), 1.40 (18H, s, 6CH$_3$).

$^{13}$C NMR (DMSO-$d_6$, 270 MHz): δ=155.3, 143.9, 129.4, 127.8, 127.4, 101.0, 70.5, 57.6, 36.0, 32.3, 28.5.

Example 17

Synthesis of α-[4-(2-Methoxy)ethoxymethoxy-3,5-di-tert-butylphenyl]-N-tert-butylnitrone The title compound was prepared in benzene with 3,5-di-tert-butyl-4-(2-methoxy)ethoxymethoxybenzaldehyde and tert-butylhydroxylamine using the procedure described in Example 16. The title compound was isolated (70.1% yield) as a white solid, m.p. 169.6–173.5° C.

Spectroscopic data were as follows:

$^1$H NMR (DMSO-$d_6$, 270 MHz): δ=8.38 (2H, s, phenyl H), 7.80 (1H, s, nitronyl H), 4.91 (2H, s, OCH$_2$), 3.87 (2H, m, J=4.76 Hz, ethoxy OCH$_2$), 3.54 (2H, m, J=4.76 Hz, OCH$_2$), 3.28 (3H, s, OCH$_3$), 1.49 (9H, s, 3CH$_3$), 1.40 (18H, s, 6CH$_3$).

$^{13}$C NMR (DMSO-$d_6$, 270 MHz): δ=155.3, 143.9, 129.4, 127.8, 127.4, 100.1, 71.7, 70.5, 69.3, 58.7, 36.0, 32.3, 28.5.

Examples 18–34

Using the appropriate starting materials and the procedures described herein, the following additional compounds are prepared:

18. α-(4-methoxymethoxy-3,5-di-tert-butylphenyl)-N-3-(thiomethoxy)but-1-ylnitrone (m.p. 76.7–80.0° C.); and 19. α-(4-methoxymethoxy-3,5-di-tert-butylphenyl)-N-3-thiomethoxypropylnitrone (m.p. 55–63° C.).

20. α-(4-hydroxy-3,5-di-tert-butylphenyl)-N-tert-butylnitrone (m.p. 225° C.)

21. α-(4-hydroxy-3,5-di-tert-butylphenyl)-N-tert-octylnitrone (m.p. 113–115° C.).

22. a-(4-hydroxy-3,5-dimethoxyphenyl)-N-tert-butylnitrone (m.p. 185.4° C.)

23. α-(4-hydroxy-3,5-dimethylphenyl)-N-hexylnitrone (m.p. 128° C.)
24. α-(4-hydroxy-3,5-dimethylphenyl)-N-tert-butylnitrone (m.p. 197.5–198.3° C.)
25. α-(4-hydroxy-3,5-di-tert-butylphenyl)-N-(1,1-dimethyl-2-hydroxyethyl)nitrone (m.p. 185–191° C.)
26. α-(4-hydroxy-3,5-di-tert-butylphenyl)-N-(1,1-dimethylpropyl)nitrone (m.p. 215° C.)
27. α-(4-hydroxy-3,5-di-tert-butylphenyl)-N-(1-methylethyl)nitrone (m.p. 176° C.)
28. α-(4-hydroxy-3,5-di-tert-butylphenyl)-N-benzylnitrone (m.p. 123.3° C.)
29. α-(4-methoxymethoxy-3,5-di-tert-butylphenyl)-N-cyclohexylmethylnitrone (m.p. 143.1° C.)
30. α-(4-methoxymethoxy-3,5-di-tert-butylphenyl)-N-(2-tetrahydrofuryl) nitrone (m.p. 104.4° C.)
31. α-(4-methoxymethoxy-3,5-di-tert-butylphenyl)-N-benzylnitrone (m.p. 134.2° C.)
32. α-(4-methoxy-3,5-di-tert-butylphenyl)-N-tert-butylnitrone (m.p. 223.1° C.)
33. α-(4-ethoxy-3,5-di-tert-butylphenyl)-N-tert-butylnitrone (m.p. 212.1° C.)
34. α-(4-carbethoxymethoxy-3,5-di-tert-butylphenyl)-N-tert-butylnitrone (m.p. 188° C.)

Examples I and II

In these experiments, the compounds of Examples 1–3, 16 and 20–33 were tested to determine if they treated neuropathic pain in accepted in vivo models. The results of one such in vivo model of Phenylquinone (PQ) Writhing are tabulated in Tables VI and VII.

SUMMARY

Compounds of Examples 16 and 20 were evaluated for possible neuropathic pain treating activity in an in vivo model of Phenylquinone (PQ) Writhing. After dosing 100, 30 and 10 mg/kg orally, both compounds exhibited significant ($P<0.01$ for all the 3 doses) analgesia relative to vehicle control group using Dunnett's test. Additional compounds 1–3 and 21–33 were tested at 30 mg/kg of dose. Ten out of thirteen compounds showed >30% inhibition of writhing response.

Materials and Equipment
1. Test Compound and Dosing Pattern
   The compounds of Example 20 and Example 16 administered orally at doses of 10, 30 and 100 mg/kg. Vehicle of 2% Tween 80 in distilled water was used.
2. Chemicals
   2% Tween 80, Phenylquinone (Sigma).
3. Animals
   In this study, ICR derived male mice provided by animal breeding center of MDS Panlabs Taiwan, Ltd. were used. Space allocation for 10 animals was 45×23×15 cm. Mice were housed in APEC$^R$ (Allentown Gaging, Allentown, N.J. 08501, U.S.A.) cages in a positive pressure isolation (NuAire$^R$, Mode: Nu-605, airflow velocity 50±5 ft/min, HEPA Filter) and maintained in a controlled temperature (22°–24° C.) and humidity (60%–80%) environment with 12 hour light dark cycles for at least one week in MDS Panlabs Taiwan laboratory prior to be used. Free access to standard lab chow for mice (Fwusow Industry Co., Limited, Taiwan) and tap water was granted. All aspects of this work including housing, experimentation and disposal of animals were performed in general accordance with the International Guiding Principles for Biomedical Research Involving Animals (CIOMS Publication No. ISBN 92 90360194, 1985).

Methods

The method of Siegmund, E. et al., Proc. Soc. Exp. Biol. Med. 95: 729–731, 1957, "A method for evaluating both non-narcotic and narcotic analgesics" was used. One hour after vehicle or compound administration, the number of writhes was recorded for each mouse in groups of 10 animals during a 5 to 10 minute period following 2 mg/kg. 1.p. of phenylquinone.

Groups of 10 male ICR mice weighing 22±2 gm were employed. Three doses (10, 30 and 100 mg/kg) of test substances suspended in a vehicle of 2% Tween 80 were administered per os. The control group received vehicle alone. At 60 minutes post dosing 2 mg/kg of phenyquinone (PQ) was injected intraperitoneally and the number of writhes exhibited during the following 5–10 minute period post PQ injection were recorded. The mean±SEM value of writhing number for each treatment group was then calculated and Dunnett's test was applied for comparison between vehicle and treated groups. Differences were considered significant when $P<0.01$.

Results Tables

TABLE VI

Phenylquinone (PQ) Writhing Assay Data: # of Writhes

| Compound | Dose | # Writhes (X + SEM) |
| --- | --- | --- |
| Vehicle (2% Tween 80/D.W.) | 20 ml/kg | 20.8 ± 0.7 |
| Compound of Example 20 | 10 ml/kg | 3.1 ± 1.4** |
|  | 30 ml/kg | 0.9 ± 0.5** |
|  | 100 ml/kg | 0.3 ± 0.2** |
| Compound of Example 16 | 10 ml/kg | 14.9 ± 1.2** |
|  | 30 ml/kg | 3.9 ± 1.3** |
|  | 100 ml/kg | 1.3 ± 0.6** |

These data are presented in bar-graph form in FIG. 1

Additional compounds were evaluated for possible neuropathic pain treating activity in an in vivo model of phenylquinone (PQ) writhing.

Materials and Animals

Test compounds were prepared as a suspension in 1% methyl cellulose and dosed orally at a dose of 30 mg/kg to male Swiss Webster mice weighing between 15 and 25 g with 10 mice per group. Test compounds was given 1 hour before the injection of phenylquinone. Phenylquinone (Sigma) was injected intraperitoneally at a dose of 2 mg/kg. After a 5 minute acclimation period, the number of writhes was counted for a 5 minute observation period for each mouse. The total number of writhes for each test compound was compared with a vehicle group. Results were expressed as % inhibition compared to the vehicle treated group means (Table VII).

TABLE VII

Phenylquinone (PQ) Writhing Assay Data: % Inhibition of Writhing Response

| No. | Compound Name | % Inhibition of Writhing Response |
|---|---|---|
|   | Indomethacin (Standard) | 93 (3 mg/kg) |
|   | Dexamethasone (Standard) | 62 (1 mg/kg) |
| 1 | "a-(4-Acetoxy-3,5-di-tert-butylphenyl)-N-tert-butylnitrone | 65 |
| 2 | a-(4-Isobutanoyl-3,5-di-tert-butylphenyl)-N-tert-butylnitrone | 29 |
| 3 | a-(4-n-Butanoyl-3,5-di-tert-butylphenyl)-N-tert-butylnitrone | 62 |
| 20 | a-(4-hydroxy-3,5-di-tert-butylphenyl)-N-tert-butylnitrone | 62 |
| 21 | a-(4-hydroxy-3,5-di-tert-butylphenyl)-N-tert-octylnitrone | 30 |
| 22 | a-(4-hydroxy-3,5-dimethoxyphenyl)-N-tert-butylnitrone | 32 |
| 23 | a-(4-hydroxy-3,5-dimethylphenyl)-N-hexylnitrone | 47 |
| 24 | a-(4-hydroxy-3,5-dimethylphenyl)-N-tert-butylnitrone | 23 |
| 25 | a-(4-hydroxy-3,5-di-tert-butylphenyl)-N-(1,1 -dimethyl-2-hydroxyethyl)nitrone | 30 |
| 26 | a-(4-hydroxy-3,5-di-tert-butylphenyl)-N-(1,1-dimethylpropyl)lnitrone | 48 |
| 27 | a-(4-hydroxy-3,5-di-tert-butylphenyl)-N-(1-methylethyl)lnitrone | 30 |
| 28 | a-(4-hydroxy-3,5-di-tert-butylphenyl)-N-benzylnitrone | 45 |
| 32 | α-(4-methoxy-3,5-di-tert-butylphenyl)-N-tert-butylnitrone | 38 |
| 33 | α-(4-ethoxy-3,5-di-tert-butylphenyl)-N-tert-butylnitrone | 4 |

Figure 2:
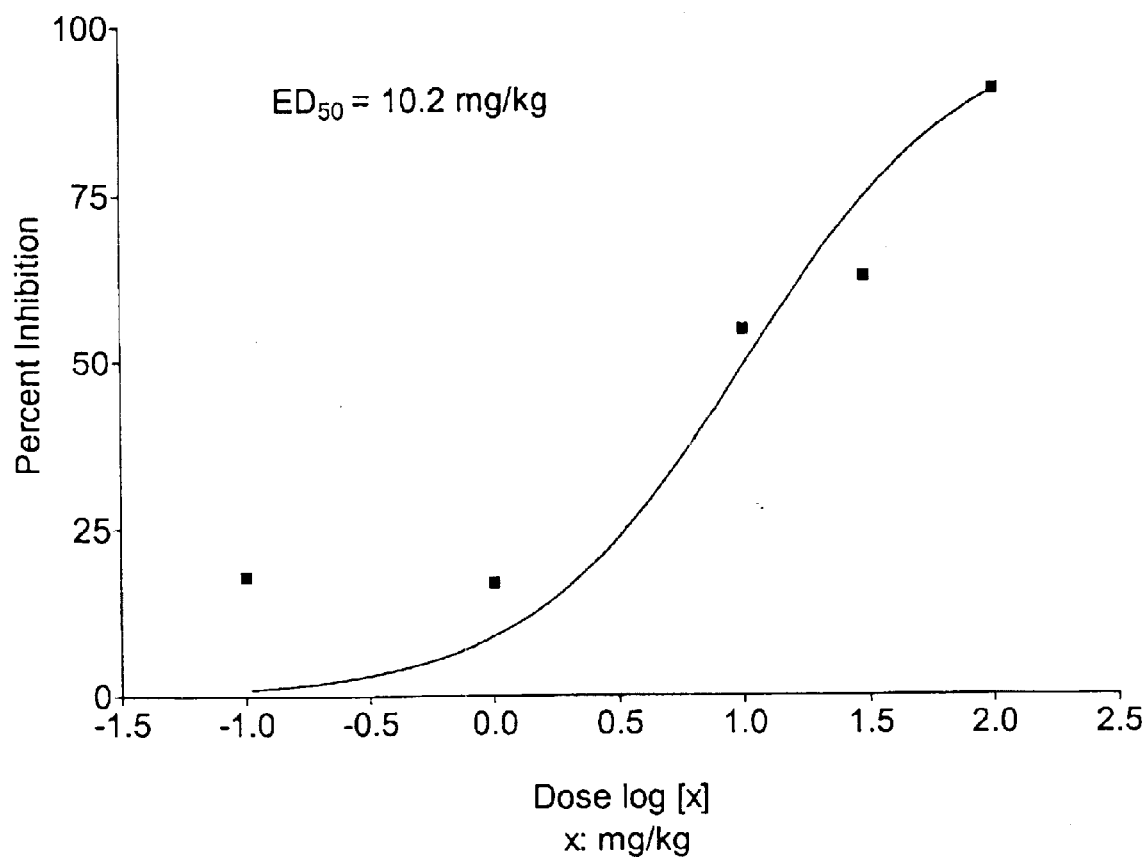
FIG. 2 is a dose response curve for test compound of Example 1 ($ED_{50}$ 2.7 mg/kg) illustrating the effectiveness of the present invention in an in vivo model for neuropathic pain, the phenylquinone writhing assay.

In related experiment, a dose response relationship was established for the compound of Example 1 using the same experimental protocl as above. Treatment of mice with the test compound 1 at various doses established an oral ED50 of 2.7 mg/kg. This is shown graphically in FIG. 2. Significant activity was also established for Examples 23 and 25 in this model.

Example III

An additional model for neuropathic pain in which the method of the invention shows activity is the widely accepted model of Bennett, G. J. and Xie, Y., PAIN 33 (1988) 87–107 which describes a peripheral mononeuropathy in neuropathic pain in rats that produces pain sensations like those seen in man.

Figure 3:
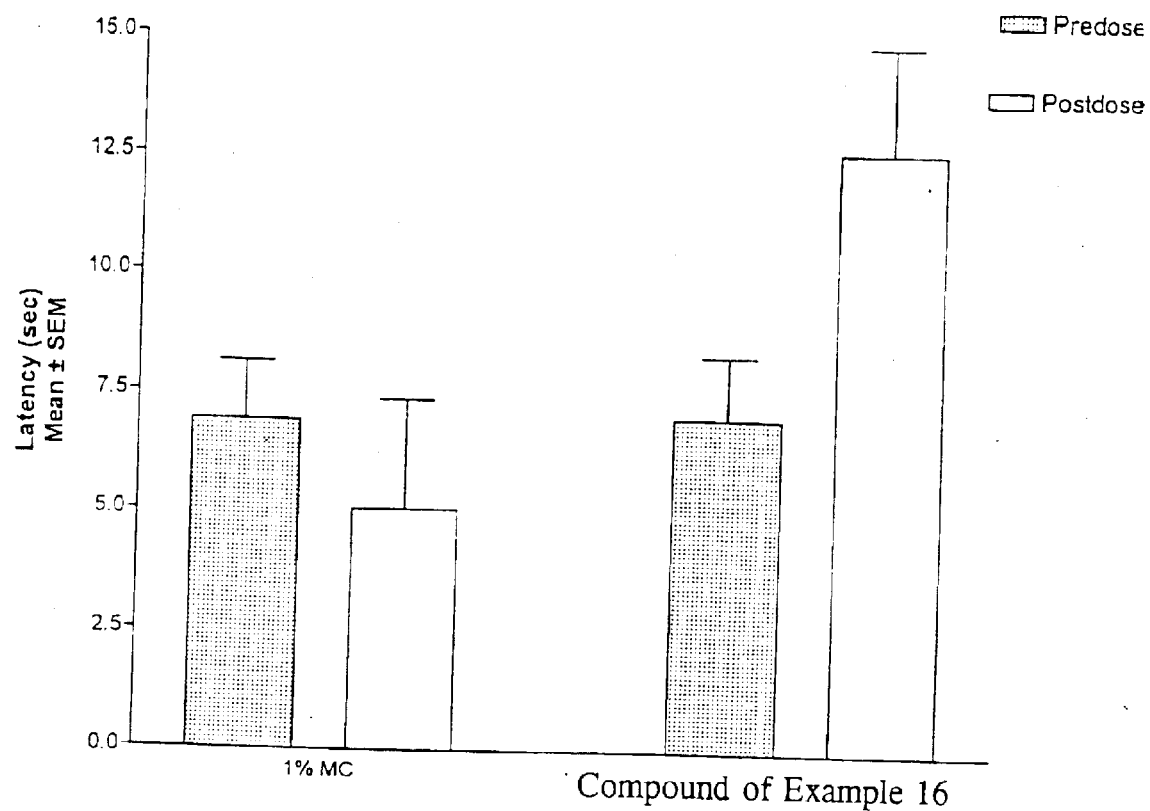
FIG. 3 is a set of bar graphs illustrating the effectiveness of the present invention in a second in vivo model for neuropathic pain, the Bennett chronic constriction assay.

This test was used to test the effectiveness of the method of the invention as follows.
Mononeuropathy in Rats
Test System
Sparague Dawley rats
Method The peripheral mononeuropathy was induced by loose ligation of the sciatic nerve in anaesthetized rats. Ten days later, the nociceptive threshold was evaluated. The test compound is administered orally 1 hour prior to pain measurement. For comparison, a predose threshold was determined and a control experiment using 1% methyl cellulose was run. Rats exhibiting latency to cold stimulus were treated with 1% MC vehicle and test compound (100 mg/kg, p.o.). Animals were again tested 1–2 hrs post-dose. Predose and postdose average scores are determined. The results of the study for the test compound of Example 16 are given in FIG. 3 and show that the method is effective.

Figure 4:
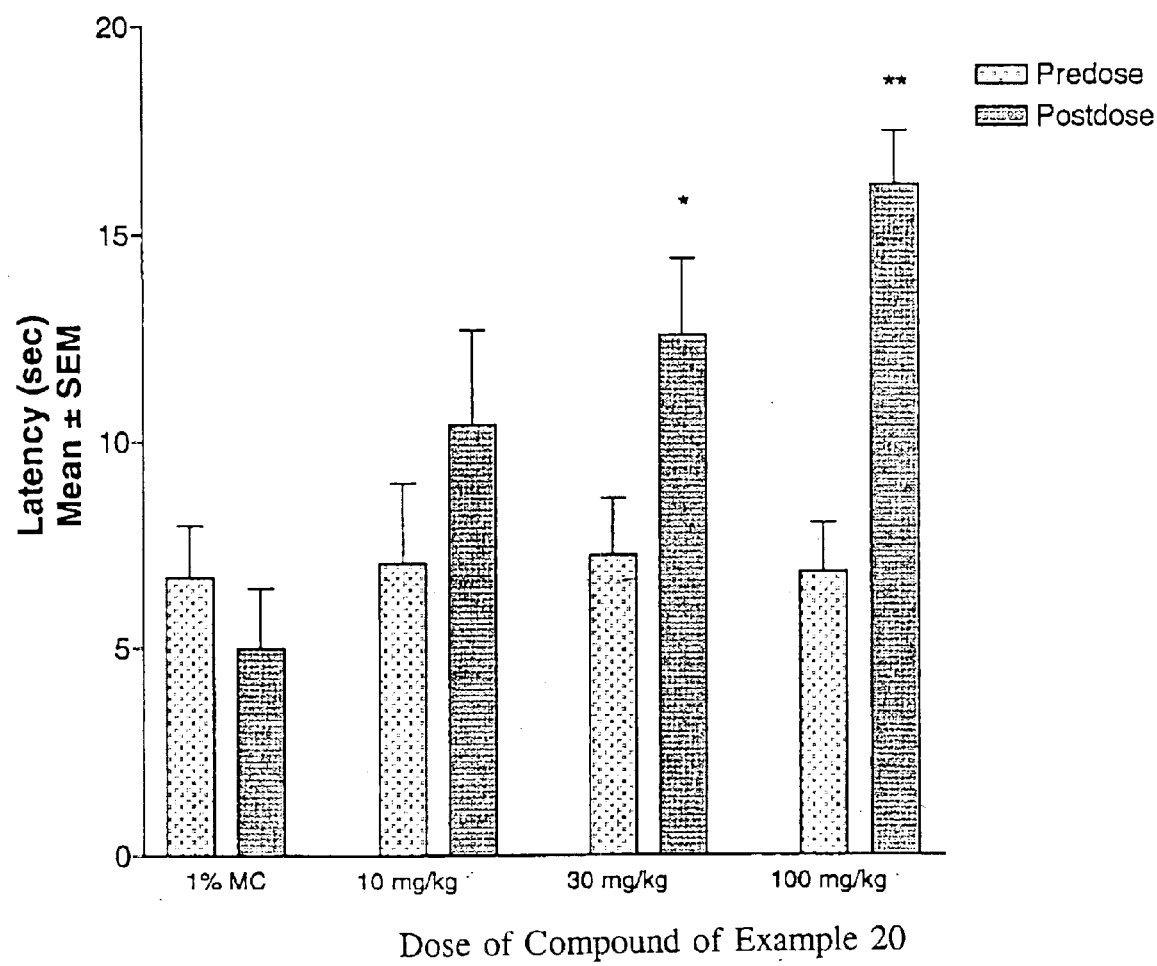
FIG. 4 is a set of bar graphs showing a dose response in a cold allodynia assay using the method of the invention.

In a related experiment a dose-response relationship for the compound of Example 20 was determined using the same experimental protocol. Treatment of CCI rats with the compound of Example 20 at various doses increased latency in the cold allodynia assay. Chronic constriction injury (CCI) rats exhibiting latency to cold stimulus were treated with 1% MC vehicle and different concentrations of the test compound (10, 30, 100 mg/kg, p.o.). Animals were again tested 1 hr post-dose. Predose and postdose average scores are shown in the FIG. 4. One-Way ANOVA indicated significant postdose latency score over vehicle (n=10), in animals treated with the test compound at 30 mg/kg (*p<0.05 vs. vehicle postdose, n=7–8, Dunnett's test post hoc) and 100/kg (**p<0.01 vs. vehicle postdose, n=7–8, Dunnett's test post hoc).

Example IV

The compound of Example 20 was further tested in a Hargreaves test, another accepted model for neuropathic pain.

Rats were tested on Day 20 in Type II collagen assay. Significant activity was obtained at doses of 10–100 mg/kgm. The $ED_{50}$ was calculated to be 6.25 mg/kg, po. Two hours after the $1^{st}$ dose of drug on Day 20, animals were placed on a Hargreaves apparatus glass table. A high intensity light was placed under the one hind paw and illuminated, thus creating heat. At the same time, a clock was started. The light turned off, and the clock simultaneously stopped when the animal removed the paw. The time the rat is able to withstand the hear is considered withdrawal latency.

Figure 5:
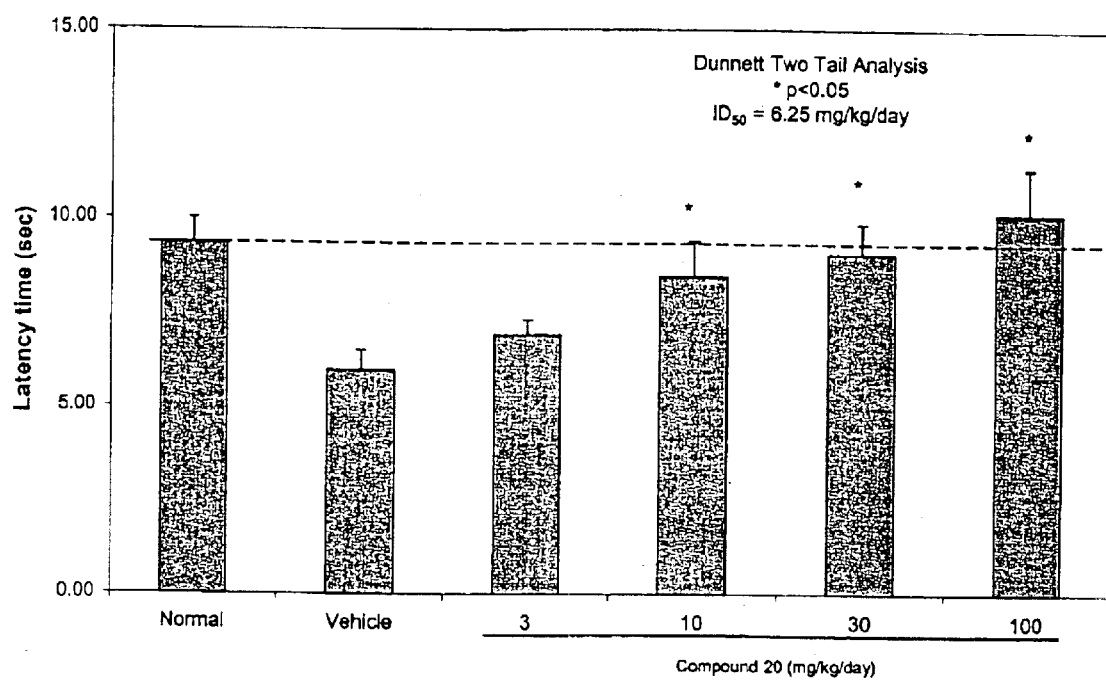
FIG. 5 is a set of bar graphs illustrating the effectiveness of the present invention in a third in vivo model for neuropathic pain, the Hargreaves Test.

The results of these tests are given in FIG. 5 and show that the compound does exhibit activity in this neuropathic pain model.

Stelzer, Z, Dubner, R. and Shir, Y., PAIN 43 (1990) 205–218 disclosed another model in which partial sciatic nerve injury induces neuropathic pain in rats. The method of this invention could be evaluated in this test, as well.

COMPARATIVE EXAMPLE

An additional study was carried out which showed that the treatment being carried out was treating neuropathic pain and not merely providing general analgesia.
Summary The purpose of the experiment was to determine if the compound of Example 16 has significant general analgesic activity as opposed to the desired activity against neuropathic pain. Test compound, 1% methylcellulose as a vehicle and morphine sulfate as a positive standard were tested for analgesic activity using a rat hot-plate assay (55° C.) of Eddy and Leimbach (J. Pharmacol. Ep. Ther 107; 385–393 (1953)) to evaluate nociceptive responses.
Experimental Design Rats (Sprague-Dawley, 217–227 g.) were used with 10 animals per group. Two pre-dose trials to nociceptive responses were determined before administration of compounds. Sixty minutes prior to testing, rats were dosed with either test compound (100 mg/kg, p.), as a suspension in 1% methylcellulose, or 1% methylcellulose as a vehicle (1 mg/kg, p.). thirty minutes prior to testing, a third group was dosed with morphine sulfate (4.0 mg/kg, 2.0 ml/kg, sc) to test for nociceptive responses using a hot plate. Latency to rear paw licking response or jump response (1) was recorded using an electronic timer. The cut-off time for either response was 30 seconds. Statistical significance was assessed for paired groups using a Turkey test and between non-paired groups using Kruskal-Wallis test. A probability value of <0.05 was identified as statistically significant.

Results

There were no statistically significant differences between the mean pre-dose latencies for any of the three treatment groups. The administration of 1% methylcellulose as a vehicle did not significantly affect the hot-plate assay mean latency; 9.2±1.2 seconds (mean±SEM) as compared to the pre-dose mean latency of 10.1±1.1 seconds (mean±SEM). Under these test conditions, morphine sulfate significantly increased the mean latency to jump/hind paw licking response compare with pre-dose; 24.3±2.3 seconds (mean±SEM) versus 9.9±1.0 seconds (mean±SEM), respectively, (P<0.001, Turkey test). Test compound (100 mg/kg) administered orally did not significantly affect hot-plate latency; 9.7±1.0 seconds (mean±SEM) as compared to the pre-dose value of 7.9±1.0 seconds (mean±SEM), suggesting that the test compound at 100 mg/kg does not affect the nociceptive response as determined by the hot-plate assay.

Figure 6:
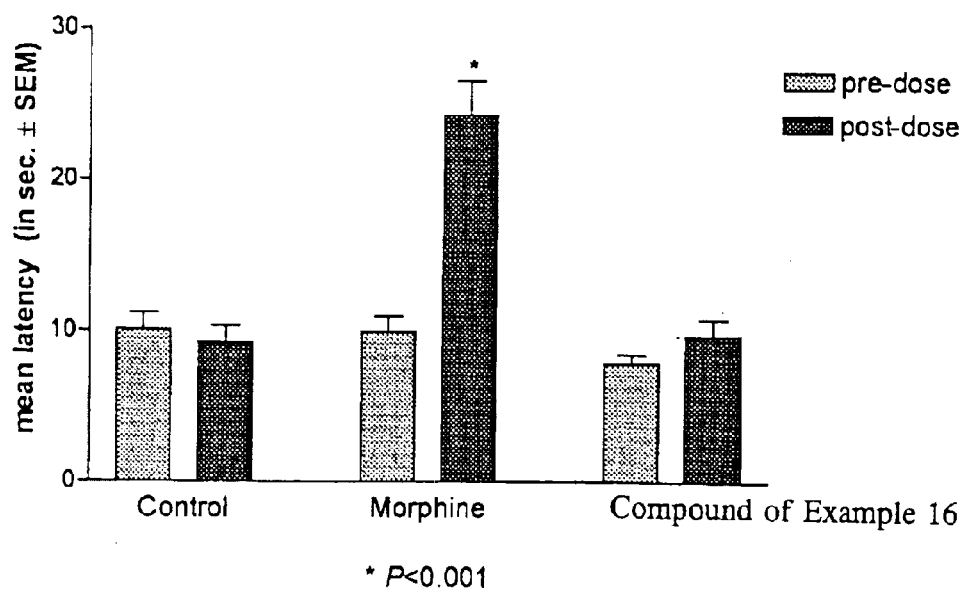
FIG. 6 is a set of bar graphs showing, for comparison purposes, that the present method is specific for neuropathic pain and is not active in the treatment of other non-neuropathic pain condition.

Those test results are summarized in FIG. 6.

From the foregoing description, various modifications and changes in the compositions and methods of this invention will occur to those skilled in the art. All such modifications coming within the scope of the appended claims are intended to be included therein.

What is claimed is:

1. A method for treating neuropathic pain in a patient comprising administering an effective neuropathic pain-treating dose of a pharmaceutical composition comprising a compound of formula I:

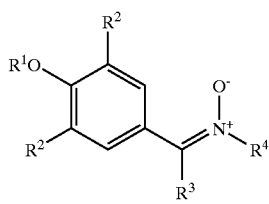

I wherein
$R^1$ is

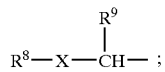

each $R^2$ is independently selected from a group of the formula:

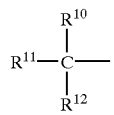

$R^3$ is selected from the group consisting of hydrogen, alkyl, cycloalkyl and aryl;
$R^4$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;
$R^8$ is selected from the group consisting of alkyl, substituted alkyl, alkenyl, substituted alkenyl, alkynyl, substituted alkynyl, cycloalkyl, substituted cycloalkyl, cycloalkenyl and substituted cycloalkenyl;
$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl and substituted cycloalkenyl; or $R^8$ and $R^9$ can be joined to form an alkylene or substituted alkylene group having from 2 to 10 carbon atoms;
$R^{10}$ is selected from the group consisting of hydrogen, lower alkyl and lower cycloalkyl; or $R^1$ and $R^{10}$ can be joined to form an alkylene, substituted alkylene, —C(O)—S(O)— or —S(O)$_2$— group;
$R^{11}$ and $R^{12}$ are independently selected from the group consisting of lower alkyl and lower cycloalkyl; or $R^{11}$ and $R^{12}$ can be joined to form an alkylene group having from 2 to 10 carbon atoms; and
X is oxygen, sulfur, —S(O)— or —S(O)$_2$—,
or a pharmaceutically-acceptable salt thereof.

2. The method of claim 1 wherein X is oxygen.

3. The method of claim 2 wherein $R^3$ is hydrogen or lower alkyl.

4. The method of claim 3 wherein $R^3$ is hydrogen.

5. The method of claim 4 wherein $R^4$ is selected from the group consisting of alkyl, substituted alkyl and cycloalkyl.

6. The method of claim 5 wherein $R^4$ is selected from the group consisting of methyl, n-propyl, isopropyl, 1-hydroxy-2-methylprop-2-yl, n-butyl, tert-butyl, 3-thiomethylpropyl, 3-(thiomethoxy)but-1-yl, cyclohexyl, 4-trifluoromethybenzyl and 3,4,5-trimethoxybenzyl.

7. The method of claim 4 wherein X is oxygen; $R^9$ is hydrogen; and $R^8$ is alkyl or alkoxyalkyl.

8. The method of claim 7 wherein $R^8$ is selected from the group consisting of methyl and methoxyethyl.

9. The method of claim 4 wherein $R^{10}$, $R^{11}$ and $R^{12}$ are methyl.

10. The method of claim 9 wherein $R^{10}$, $R^{11}$ and $R^{12}$ are methyl.

11. The method of claim 1 wherein the compound is of formula IV:

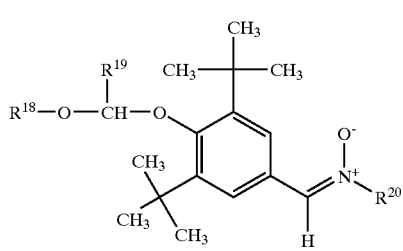

IV wherein
$R^{18}$ is selected from the group consisting of alkyl, substituted alkyl, cycloalykl and substituted cycloalkyl;
$R^{19}$ is selected from the group consisting of hydrogen, alkyl, substituted alkyl, cycloalkyl and substituted cyloalkyl; or $R^{18}$ and $R^{19}$ can be joined to form an alkylene or substituted alkylene group having from 2 to 10 carbon atoms;
$R^{20}$ is selected from the group consisting of alkyl, substituted alkyl, cycloalkyl and substituted cycloalkyl; or pharmaceutically-acceptable salts thereof.

12. The method of claim 11 wherein $R^{19}$ is hydrogen and $R^{18}$ is alkyl or alkoxyalkyl.

13. The method of claim 12 wherein $R^{18}$ is methyl or methoxyethyl.

14. The method of claim 11 wherein $R^{20}$ is selected from the group consisting of alkyl, substituted alkyl and cycloalkyl.

15. The method of claim 14 wherein $R^{20}$ is selected from the group consisting of methyl, n-propyl, isopropyl, 1-hydroxy-2-methylprop-2-yl, n-butyl, tert-butyl, 3-thiomethylpropyl, 3-(thiomethoxy)but-1-yl, cyclohexyl, 4-trifluoromethybenzyl and 3,4,5-trimethoxybenzyl.

16. The method of claim 1 wherein the compound is selected from the group consisting of:

α-(4-methoxymethoxy-3,5-di-tert-butylphenyl)-N-tert-butlynitrone

α-[4-(2-methoxy)ethoxymethoxy-3,5-di-tert-butylphenyl]-N-tert-butylnitrone

α-(4-methoxymethoxy-3,5-di-tert-butylphenyl)-N-3-(thiomethoxy)but-1-ylnitrone

α-(4-methoxymethoxy-3,5-di-tert-butylphenyl)-N-3-thiomethoxypropylnitrone and pharmaceutically acceptable salts thereof.

* * * * *